US012644874B1

(12) United States Patent
MacMullin et al.

(10) Patent No.: US 12,644,874 B1
(45) Date of Patent: Jun. 2, 2026

(54) METHANE EMISSION ASSESSMENT USING MOBILE SURVEYS OVER TIME IN A TARGET AREA

(71) Applicant: Picarro Inc., Santa Clara, CA (US)

(72) Inventors: Sean MacMullin, Raleigh, NC (US); Francois-Xavier Rongere, Fremont, CA (US); Noah Randolph, San Carlos, CA (US); Alan Ly, San Francisco, CA (US)

(73) Assignee: Picarro Inc., Santa Clara, CA (US)

( * ) Notice: Subject to any disclaimer, the term of this patent is extended or adjusted under 35 U.S.C. 154(b) by 292 days.

(21) Appl. No.: 18/648,344

(22) Filed: Apr. 27, 2024

Related U.S. Application Data

(60) Provisional application No. 63/620,739, filed on Jan. 12, 2024.

(51) Int. Cl.
G01N 33/00 (2006.01)
G01M 3/00 (2006.01)

(52) U.S. Cl.
CPC ........ G01N 33/0067 (2013.01); G01M 3/007 (2013.01)

(58) Field of Classification Search
CPC ......... G01M 3/16; G01M 3/20; G01M 3/205; G01M 3/26; G01M 3/18; G01M 3/22; G01M 3/38; G01M 3/228; G01M 3/207; G01M 3/00; G01M 3/002; G01M 3/202; G01M 3/229; G01M 3/02; G01M 3/24; G01M 15/10; G01M 15/102; G01M 15/106; G01M 3/045; G01N 33/0009; G01N 33/0034; G01N 33/0075; G01N 33/225; G01N 33/0008; G01N 33/0063; G01N 33/0067; G01N 2021/1793; G01N 21/3518; G01N 2021/3155; G01N 2021/3531; G01N 21/33; G01N 21/3504; G01N 1/02; G01N 1/22; G01N 1/2247; G01N 1/2252; G01N 2001/2288; G01N 2021/7786; G01N 21/25; G01N 21/64; G01N 21/643; G01N 21/783; G01N 31/223
See application file for complete search history.

(56) References Cited

U.S. PATENT DOCUMENTS

| | | | |
|---|---|---|---|
| 9,599,597 B1 | 3/2017 | Steele | |
| 10,203,311 B2 * | 2/2019 | Risk | G01P 13/02 |
| 10,386,258 B1 | 8/2019 | Steele | |
| 10,515,530 B2 * | 12/2019 | Cornwall | G01M 3/22 |
| 10,732,014 B2 | 8/2020 | MacMullin | |
| 10,877,007 B2 | 12/2020 | Steele | |
| 10,962,437 B1 * | 3/2021 | Nottrott | G01N 21/3504 |

(Continued)

FOREIGN PATENT DOCUMENTS

| | | | | |
|---|---|---|---|---|
| WO | WO-2023104528 A1 * | 6/2023 | | G01M 3/04 |
| WO | WO-2025219567 A1 * | 10/2025 | | G01M 3/04 |

*Primary Examiner* — Andre J Allen
(74) *Attorney, Agent, or Firm* — Law Office of Andrei D Popovici, PC

(57) ABSTRACT

In some embodiments, methane leak emissions are quantified accurately in natural gas distribution systems in which mobile surveys are performed on different parts of a target area over an extended reporting period (e.g. a year or more). Emission calculations depend on repair and/or mobile survey schedules, and employ temporal and/or spatial extrapolation in order to account for imperfect real-time information about system state.

21 Claims, 19 Drawing Sheets

(56)     References Cited

U.S. PATENT DOCUMENTS

| | | | |
|---|---|---|---|
| 11,525,819 B1 | 12/2022 | MacMullin | |
| 11,781,976 B2 | 10/2023 | Langland | |
| 11,933,774 B1 * | 3/2024 | MacMullin | G01M 3/04 |
| 12,163,939 B2 * | 12/2024 | Brandt | G01N 33/225 |
| 12,216,105 B2 * | 2/2025 | Nottrott | G01N 33/0047 |
| 12,372,439 B2 * | 7/2025 | Thorpe | G01N 1/2247 |
| 2006/0203248 A1 | 9/2006 | Reichardt | |
| 2016/0097713 A1 | 4/2016 | Kester | |
| 2017/0322383 A1 | 11/2017 | Bingham | |
| 2019/0340914 A1 | 11/2019 | Israelsen | |
| 2021/0140934 A1 | 5/2021 | Smith | |

* cited by examiner

54 — Authentication

56 — Gas/GPS/Wind

58 — GUI

60 — Client-Side Real-Time Data Processing

62 — Authentication

64 — Current and Historical Survey Results

66 — Reference Data (Plats, etc.)

68 — Server-Side Real-Time Data Processing

18

12

| Surface wind speed at 10 m (m/s) | Day | | | Night | |
|---|---|---|---|---|---|
| | Incoming Solar radiation | | | Cloud Cover | |
| | Strong | Moderate | Slight | Thinly Overcast (>4/8 cloudy) | Mostly Cloudy |
| <2 | A | A-B | B | | |
| 2-3 | A-B | B | C | E | F |
| 3-5 | B | B-C | C | D | E |
| 5-6 | C | C-D | D | D | D |
| >6 | C | D | D | D | D |

FIG. 11

| | Collection area | | Total | |
|---|---|---|---|---|
| | Miles | % | Miles | % |
| Urban | 100 | 10% | 200 | 5% |
| Suburban | 400 | 40% | 1200 | 30% |
| Comm | 50 | 5% | 500 | 13% |
| Ind | 50 | 5% | 100 | 3% |
| Rural | 400 | 40% | 2000 | 50% |
| | 1000 | | 4000 | |

Determine Emissions w/o Repairs ———600

Determine Number of Repairs ———602

Determine Repairs Before Data Collection ———604

Determine Correction Due to Repairs ———606

Determine Correction Due to Missed Leaks ———608

Deteremine Corrected Emissions ———610

Nb of observed leaks for a number of repairs

METHANE EMISSION ASSESSMENT USING MOBILE SURVEYS OVER TIME IN A TARGET AREA

RELATED APPLICATION DATA

This application claims the benefit of the filing date of U.S. Provisional Patent Application No. 63/620,739, filed Jan. 12, 2024, entitled "Methane Emission Assessment Using Mobile Surveys Over Time in a Target Area," which is incorporated herein by reference.

BACKGROUND

The invention relates to systems and methods for detecting gas leaks such as methane leaks, and for assessing such leaks over an extended period of time (e.g. months, years).

A common means of distributing energy around the world is by the transmission of gas, usually natural gas. In some areas of the world manufactured gasses are also transmitted for use in homes and factories. Gas is typically transmitted through underground pipelines having branches that extend into homes and other buildings for use in providing energy for space and water heating. Many thousands of miles of gas pipeline exist in virtually every major populated area. Since gas is highly combustible, gas leakage is a serious safety concern. Recently, there have been reports of serious fires or explosions caused by leakage of gas in the United States as the pipeline infrastructure becomes older. For this reason, much effort has been made to provide instrumentation for detecting small amounts of gas so that leaks can be located to permit repairs.

Conventionally, search teams are equipped with gas detectors to locate a gas leak in the immediate proximity of the detector. When a plume of gas from a leak is detected, the engineers may walk to scan the area slowly and in all directions by trial and error to find the source of the gas leak. This process may be further complicated by wind that quickly disperses the gas plume. Such a search method is time consuming and often unreliable, because the engineer walks around with little or no guidance while trying to find the source of the gas leak.

Another approach to gas leak detection is to mount a gas leak detection instrument on a moving vehicle. A natural gas detector apparatus is mounted to the vehicle so that the vehicle transports the detector apparatus over an area of interest. The apparatus is arranged such that natural gas intercepts a beam path and absorbs representative wavelengths of a light beam. A receiver section receives a portion of the light beam onto an electro-optical etalon for detecting the gas. Although a moving vehicle may cover more ground than a surveyor on foot, there is still the problem of locating the gas leak source (e.g., a broken pipe) if a plume of gas is detected from the vehicle.

U.S. Pat. Nos. 10,775,262, 10,466,132, 9,719,879 and 9,645,039, herein incorporated by reference, describe a number of mobile survey methods, including survey methods including displaying leak indicators that graphically indicate wind speed and/or variability (denoted LISA therein), and field-of-view (FOV) graphical indicators displaying areas deemed to have been surveyed. Areas where a leak would have been identified (if present) generally depend on the survey path and its relationship to wind direction and/or variability during the respective survey(s). Such areas are generally upwind from the survey path, and are deeper in the presence of stronger winds.

U.S. Pat. No. 10,732,014, herein incorporated by reference, describes a number of methods of quantifying gas plume flux values for leaks by, inter alia, collecting line scans of concentration data and estimating gas plume extents.

U.S. Pat. Nos. 11,525,819 and 10,948,471, herein incorporated by reference, describe ranking gas leaks by hazard level. A risk model is applied to survey concentration and location data to sort identified leaks by hazard level.

Methods such as those described above make it easier for operators of natural gas distribution infrastructure (e.g. power companies) to maintain their infrastructure and prioritize repairs. As the amount of available survey data increases, larger amounts of data are available to network operators for making maintenance decisions and optimizing efficiency.

SUMMARY

According to one aspect, a system comprises at least one hardware processor and a memory storing instructions which, when executed, cause the system to: receive collected data including gas concentration and location values collected by a vehicle-borne gas concentration measurement device configured to perform a sequence of geospatially-referenced mobile gas concentration measurements along one or more survey paths within a target area; identify a set of gas leaks within the target area according to the collected data; and determine a total gas emission quantity emitted within the target area over a time period encompassing the sequence of gas concentration measurements, wherein determining the total gas emission quantity comprises performing a temporal extrapolation of gas emission quantity over at least part of the time period encompassing the sequence of gas concentration measurements.

According to another aspect, a method comprises employing a system comprising at least one hardware processor and a memory storing instructions to: receive collected data including gas concentration and location values collected by a vehicle-borne gas concentration measurement device configured to perform a sequence of geospatially-referenced mobile gas concentration measurements along one or more survey paths within a target area; identify a set of gas leaks within the target area according to the collected data; and determine a total gas emission quantity emitted within the target area over a time period encompassing the sequence of gas concentration measurements, wherein determining the total gas emission quantity comprises performing a temporal extrapolation of gas emission quantity over at least part of the time period encompassing the sequence of gas concentration measurements.

According to another aspect, a non-transitory computer-readable medium encodes instructions which, when executed by at least one hardware processor of a computer system, cause the computer system to: receive collected data including gas concentration and location values collected by a vehicle-borne gas concentration measurement device configured to perform a sequence of geospatially-referenced mobile gas concentration measurements along one or more survey paths within a target area; identify a set of gas leaks within the target area according to the collected data; and determine a total gas emission quantity emitted within the target area over a time period encompassing the sequence of gas concentration measurements, wherein determining the total gas emission quantity comprises performing a temporal extrapolation of gas emission quantity over at least part of the time period encompassing the sequence of gas concentration measurements.

BRIEF DESCRIPTION OF THE DRAWINGS

The foregoing aspects and advantages of the present invention will become better understood upon reading the following detailed description and upon reference to the drawings where:

FIG. 11 is a table of dispersion coefficients for various atmospheric conditions according to some embodiments of the present invention.

DETAILED DESCRIPTION

Apparatus and methods described herein may include or employ one or more interconnected computer systems such as servers, personal computers and/or mobile communication devices, each comprising one or more processors and associated memory, storage, input and display devices. Such computer systems may run software implementing methods described herein when executed on hardware. In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass storage (non-transitory) media such as magnetic, optic, and semiconductor media (e.g. hard drives, optical disks, flash memory, DRAM), as well as communications links such as conductive cables and fiber optic links. According to some embodiments, the present invention provides, inter alia, computer systems programmed to perform the methods described herein, as well as computer-readable media encoding instructions to perform the methods described herein.

Figure 1:
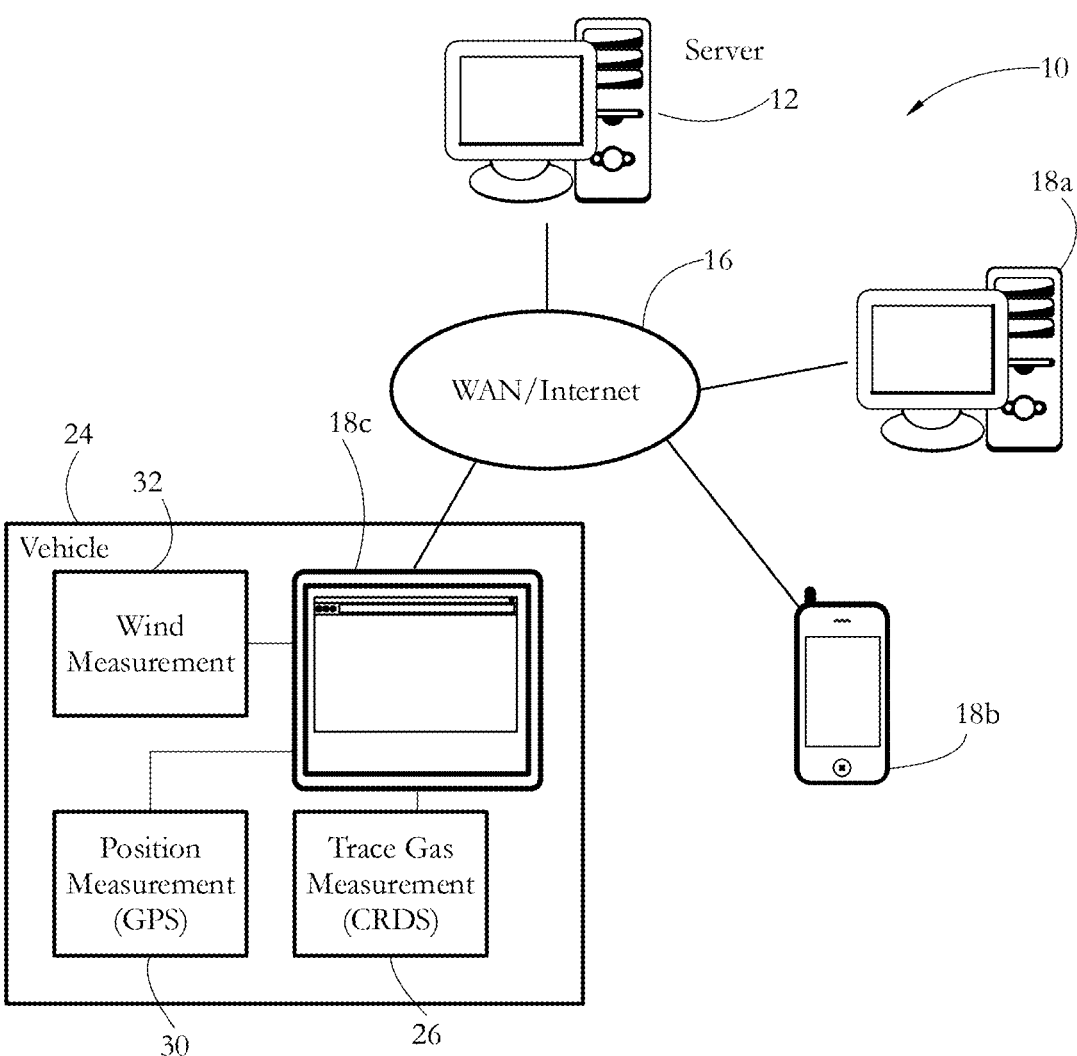
FIG. 1 shows a gas leak detection apparatus according to some embodiments of the present invention.

FIG. 1 shows a gas leak detection system 10 according to some embodiments of the present invention. System 10 comprises a service provider server computer system 12 and a set of client computer systems 18a-c all connected through a wide area network 16 such as the Internet. Client computer systems 18a-c may be personal computers, laptops, smartphones, tablet computers and the like. A vehicle 24 such as an automobile may be used to carry at least some client computer systems (e.g. an exemplary client computer system 18c) and associated hardware including a mobile gas measurement device 26, a location/GPS measurement device 30, and a wind measurement device 32. In a preferred embodiment, the mobile gas measurement device 26 may be a Picarro analyzer using Wavelength-Scanned Cavity Ring Down Spectroscopy (CRDS), available from Picarro, Inc., Santa Clara, CA. Such analyzers may be capable of detecting trace amounts of gases such as methane, acetylene, carbon monoxide, carbon dioxide, hydrogen sulfide, and/or water. In particular applications suited for detection of natural gas leaks, a Picarro G2203 analyzer capable of detecting methane concentration variations of 3 ppb may be used. Wind measurement device 32 may include a wind anemometer and a wind direction detector (e.g. wind vane). GPS measurement device 30 may be a stand-alone device or a device built into client computer system 18c.

Figure 2:
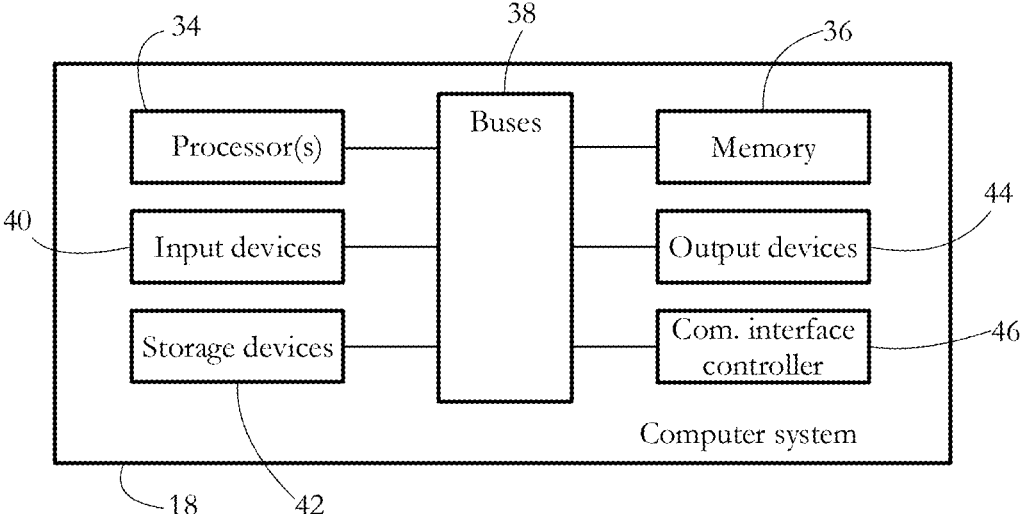
FIG. 2 illustrates hardware components of a computer system according to some embodiments of the present invention.

FIG. 2 schematically illustrates a plurality of hardware components that each computer system 18 may include. Such computer systems may be devices capable of web browsing and have access to remotely-hosted protected websites, such as desktop, laptop, tablet computer devices, or mobile phones such as smartphones. In some embodiments, computer system 18 comprises one or more processors 34, a memory unit 36, a set of input devices 40, a set of output devices 44, a set of storage devices 42, and a communication interface controller 46, all connected by a set of buses 38. In some embodiments, processor 34 comprises a physical device, such as a multi-core integrated circuit, configured to execute computational and/or logical operations with a set of signals and/or data. In some embodiments, such logical operations are delivered to processor 34 in the form of a sequence of processor instructions (e.g. machine code or other type of software). Memory unit 36 may comprise random-access memory (RAM) storing instructions and operands accessed and/or generated by processor 34. Input devices 40 may include touch-sensitive interfaces, computer keyboards and mice, among others, allowing a user to introduce data and/or instructions into system 18. Output devices 44 may include display devices such as monitors. In some embodiments, input devices 40 and output devices 44 may share a common piece of hardware, as in the case of touch-screen devices. Storage devices 42 include computer-readable media enabling the storage, reading, and writing of software instructions and/or data. Exemplary storage devices 42 include magnetic and optical disks and flash memory devices, as well as removable media such as CD and/or DVD disks and drives. Communication interface controller 46 enables system 18 to connect to a computer network and/or to other machines/ computer systems. Typical communication interface controllers 46 include network adapters. Buses 38 collectively represent the plurality of system, peripheral, and chipset buses, and/or all other circuitry enabling the inter-communication of devices 34-46 of computer system 18.

Figure 3:
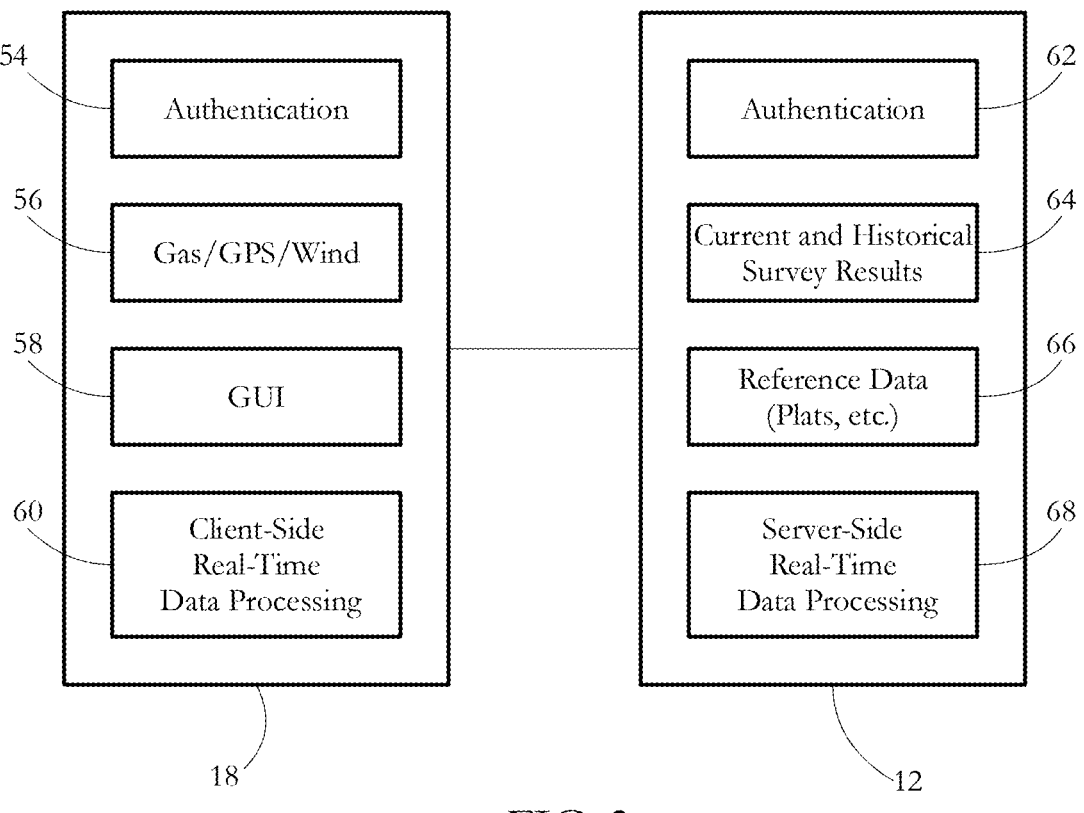
FIG. 3 shows a number of application or modules running on a client computer system and a corresponding server computer system according to some embodiments of the present invention.

FIG. 3 shows a number of applications or modules running on an exemplary client computer system 18 and corresponding server computer system 12. Authentication applications 54, 62 are used to establish secure communications between computer systems 12, 18, allowing client computer system 18 selective access to the data of a particular customer or user account. A client data collection module 56 collects real-time gas concentration, location data such as global positioning system (GPS) data, as well as wind speed and wind direction data. A graphical user interface (GUI) module 58 is used to receive user input and display survey results and other GUI displays to system users. A client-side real-time data processing module 60 may be used to perform at least some of the data processing described herein to generate survey results from input data. Data processing may also be performed by a server-side data processing module 68. Server computer system 12 also maintains one or more application modules and/or associated data structures storing current and past survey results 64, as well as application modules and/or data structures storing reference data 66 such as plats indicating the geographic locations of natural gas pipelines.

In some embodiments, surveys are performed and natural gas leak emissions are quantified as described in the above-incorporated US Patents. Exemplary survey and emission quantification methods are described below with reference to FIGS. 4-12.

Performing Mobile Surveys

Figure 4:
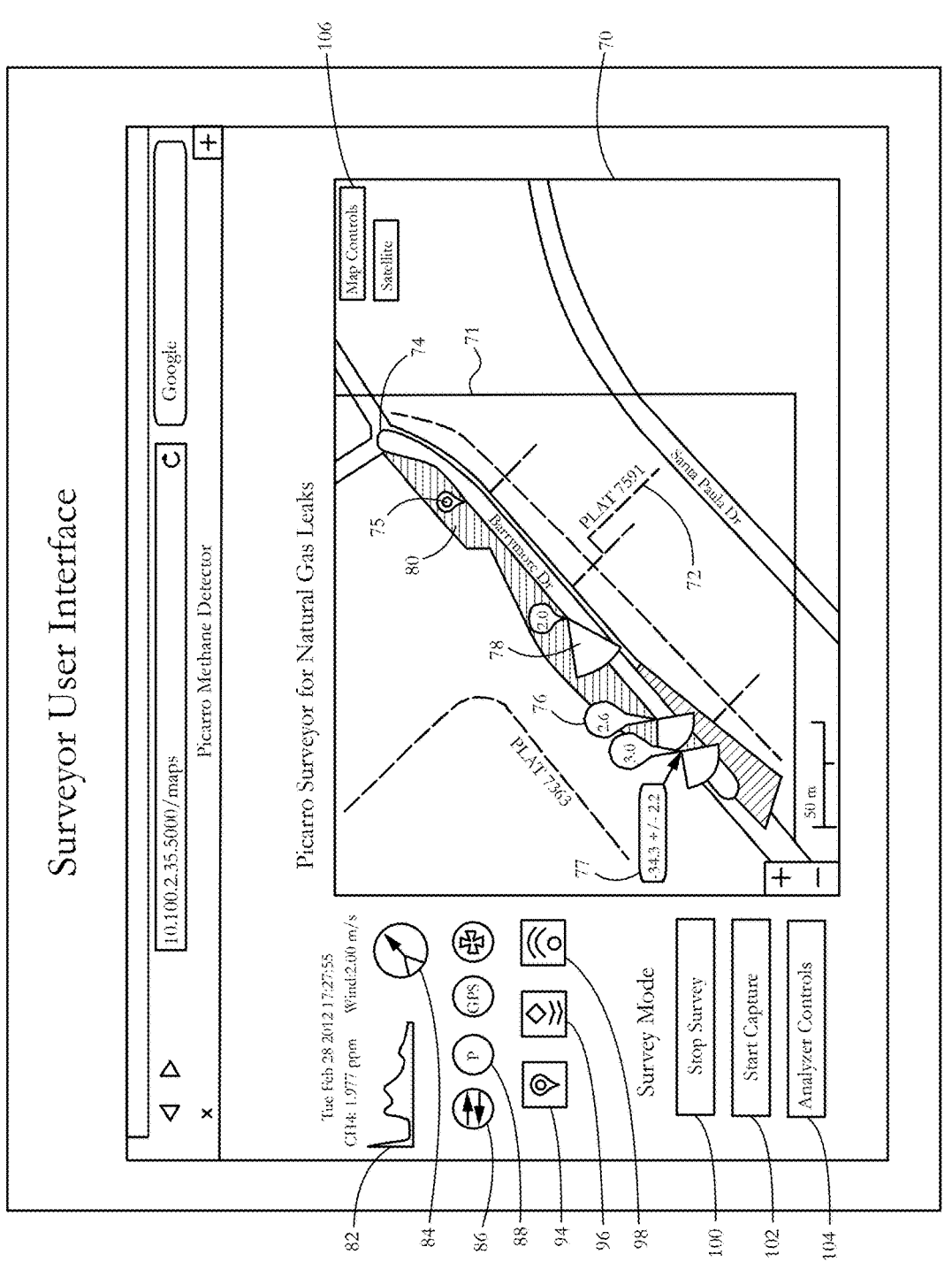
FIG. 4 is a schematic drawing of a screen shot on a graphical user interface displaying survey results on a street map according to some embodiments of the present invention.

FIG. 4 is a schematic drawing of a screen shot on a graphical user interface, displaying survey results on a street map 70 according to some embodiments of the present invention. The GUI screenshots are most preferably displayed on a client device in the vehicle, which may be connected to a server as described above. The illustrated screenshots show both exemplary user input, which may be used to control system operation, and exemplary real-time displays of collected/processed data. In the example, it includes the geo-referenced street map 70 showing plat lines 72. The plat lines 72 are preferably derived from gas company records. Map 70 may also display natural gas infrastructure features positioned at their respective locations on the map, such as pipelines (represented e.g. by lines) and/or meters and other distribution structures (represented e.g. by identifying symbols). At least part of the gas infrastructure may be highlighted (e.g. displayed using a different color and/or line thickness) if located within a survey area 80 and/or peak marker 78 (described below).

An active pipeline plat boundary 71 may also be displayed on the map 70. A user-selectable button 96 may be selected to overlay a selected pipeline plat on the map 70. Superimposed on the map 70 are one or more lines (preferably in a distinguishing color not shown in patent drawings) indicating the path 74 driven by the vehicle with the mobile gas measurement device on one or more gas survey routes. In this example, the path 74 shows the vehicle U-turned at the Y-shaped intersection. Optionally, a current location icon 75 may be overlaid on the map 70 to indicate the current surveyor location, e.g., the position of the vehicle with a gas measurement device and wind measurement device. A user-selectable button 94 may be selected to center the map 70 by current surveyor location. Also provided is a user-selectable start button 102 and stop button 100 to start/stop capturing gas for analysis. An analyzer control button 104 is user-selectable to control analyzer operations (e.g., shut down, start new trace, run isotopic analysis, etc.).

Peak markers 76 show the locations along the path 74 where peaks in the gas concentration measurements, which satisfy the conditions for being likely gas leak indications, were identified. The colors of the peak markers 76 may be used to distinguish data collected on different runs. The annotations within the peak markers 76 show the peak concentration of methane at the locations of those measurement points (e.g., 3.0, 2.6, and 2.0 parts per million). An isotopic ratio marker 77 may be overlaid on the map 70 to indicate isotopic ratio analysis output and tolerance (e.g., −34.3+/−2.2). Also displayed on the map 70 are search area indicators 78, preferably shown as a sector of a circle having a distinguishing color. Each of the search area indicators 78 indicates a search area suspected to have a gas leak source. The opening angle of the search area indicator 78 depicts the variability in the wind direction. The axis of the search area indicator 78 (preferably an axis of symmetry) indicates the likely direction to the potential gas leak source. Also displayed on the map 70 are one or more survey area indicators 80 (shown as hatched regions in FIG. 4) that indicate a survey area for a potential gas leak source. The survey area indicator 80 adjoins the path 74 and extends in a substantially upwind direction from the path. The survey area marked by each indicator 80 is preferably displayed as a colored swath overlaid or superimposed on the map 70. For example, the colored swaths may be displayed in orange and green for two runs. In preferred embodiments, the parameters of the search area indicators 78 and the survey area indicators 80 (described in greater detail with reference to FIGS. 8-11 below) are derived from measurements of the wind, the velocity of the vehicle, and optionally the prevailing atmospheric stability conditions.

Referring still to FIG. 4, the surveyor user interface also preferably includes a real-time CH₄ concentration reading 82. A wind indicator symbol 84 preferably displays real-time wind information, which may be corrected for the velocity vector of the vehicle to represent the true wind rather than the apparent wind when the vehicle is in motion. Average wind direction is preferably indicated by the direction of the arrow of the wind indicator symbol 84, while wind direction variability is indicated by the degree of open angle of the wedge extending from the bottom of the arrow. Wind speed is preferably indicated by the length of the arrow in the wind indicator symbol 84. An internet connection indicator 98 blinks when the internet connection is good. A data transfer status button 86 is user-selectable to display data transfer status (e.g., data transfer successful, intermittent data transfer, or data transfer failed). An analyzer status button 88 is user-selectable to display current analyzer status such as cavity pressure, cavity temperature, and warm box temperature. A map control button 106 is user-selectable to open a map controls window with user-selectable layer options, discussed below with reference to FIG. 7.

Figure 5:
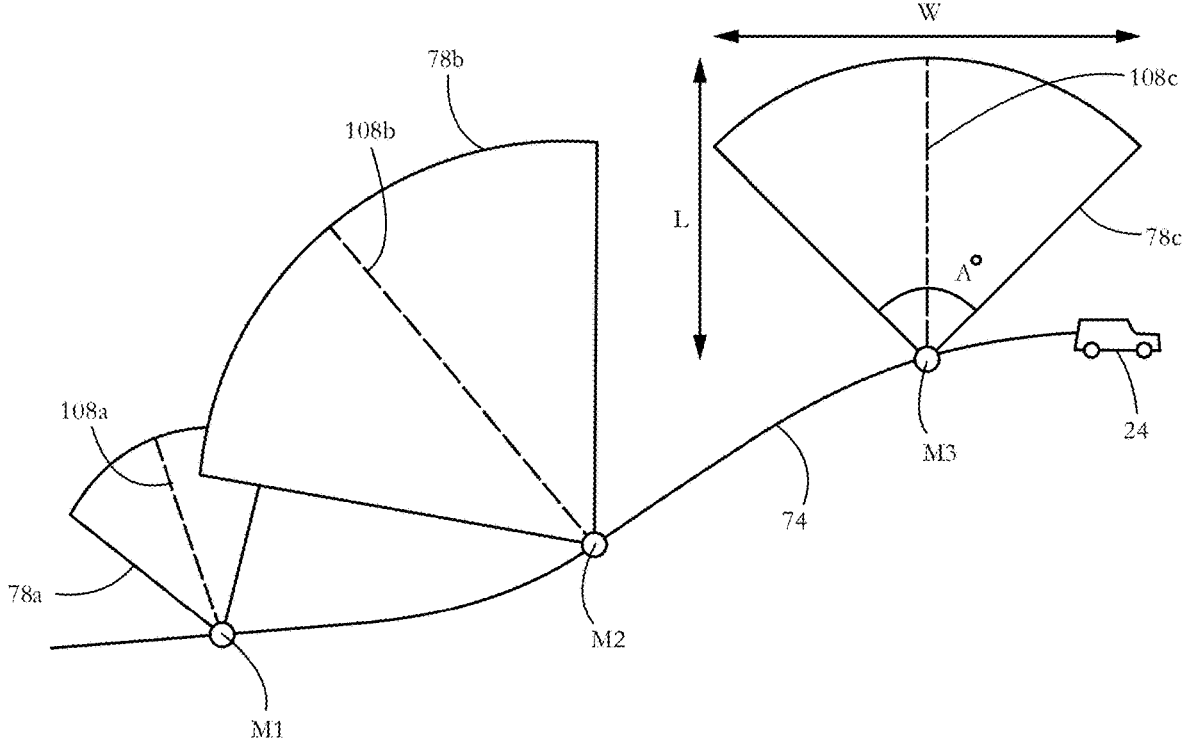
FIG. 5 is a schematic diagram of three search area indicators according to some embodiments of the present invention.

FIG. 5 is a schematic diagram of three search area indicators 78a, 78b, and 78c according to some embodiments of the present invention. Each of the search area indicators 78a, 78b, and 78c has a respective axis 108a, 108b, and 108c indicating a representative wind direction relative to a geo-referenced location of a corresponding gas concentration measurement point M1, M2, and M3. The gas concentration measurement points M1, M2, and M3 are positioned along the path 74 traveled by the vehicle 24 that carries a GPS device, a mobile gas measurement device, and wind measurement device for taking wind direction measurements and wind speed measurements. Each of the search area indicators, such as the search area indicator 78c, preferably has a width W relative to its axis 108c. The width W is indicative of a wind direction variability associated with wind direction measurements in the area of the gas concentration measurement point M3. In preferred embodiments, the width W is indicative of a variance or standard deviation of the wind direction measurements. Also in preferred embodiments, the search area indicator 78c has the shape of a sector of a circle, with the center of the circle positioned on the map at the location of the gas concentration measurement point M3. Most preferably, the angle A subtended by the sector of the circle is proportional to a standard deviation of the wind direction measurements taken at or nearby the measurement point M3. For example, the angle A may be set to a value that is twice or four times the angular standard deviation of the wind direction measurements. It is not necessary to display the gas concentration measurement points M1, M2, and M3 on the map along with the search area indicators 78a, 78b, and 78c.

Referring again to FIG. 5, the axis 108c of the search area indicator 78c is preferably an axis of symmetry and points in a representative wind direction relative to the gas concentration measurement point M3. The representative wind direction is preferably a mean, median or mode of the wind direction measurements taken at or nearby the measurement point M3, and indicates the likely direction to a potential gas leak source. The wind direction measurements may be taken from the vehicle 24 as it moves and converted to wind direction values relative to the ground (e.g., by subtracting or correcting for the velocity vector of the vehicle). In some embodiments, the axis 108c has a length L indicative of a maximum detection distance value representative of an estimated maximum distance from a potential gas leak source at which a gas leak from the source can be detected. For example, the length may be proportional to the maximum detection distance value, or proportional to a monotonically increasing function of the maximum detection distance value, such that longer maximum detection distance values are represented by longer axis lengths. In preferred embodiments, the maximum detection distance value and corresponding length L are determined according to data representative of wind speed in the search area. In some embodiments, the maximum detection distance value and the corresponding length L are determined according to data representative of atmospheric stability conditions in the search area. Each of the search area indicators 78a, 78b, and 78c may thus provide a visual indication of a likely direction and estimated distance to a potential gas leak source. Although a sector of a circle is the presently preferred shape for a search area indicator, alternative shapes for a search area indicator include, but are not limited to, a triangle, a trapezoid, or a wedge.

Figure 6:
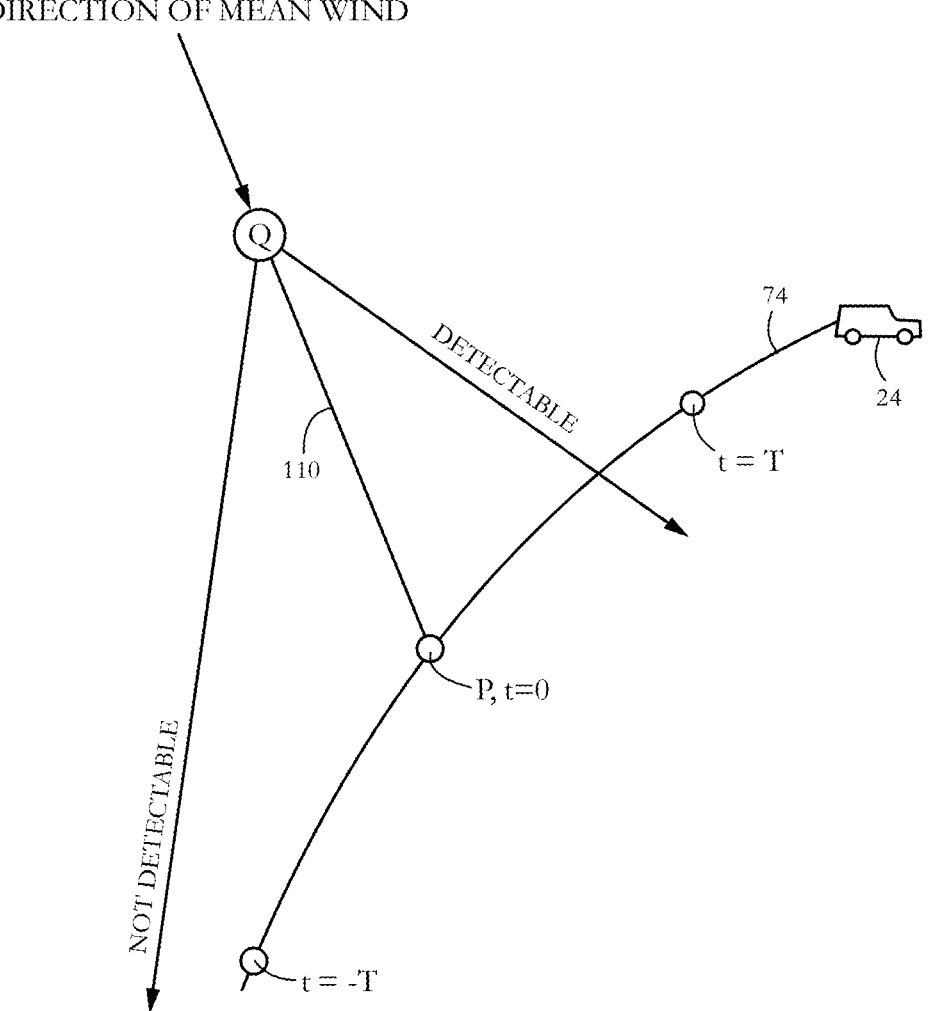
FIG. 6 is a schematic diagram illustrating wind lines relative to the path of a mobile gas measurement device for detecting or not detecting a gas leak from a potential gas leak source according to some embodiments of the present invention.

FIG. 6 is a schematic diagram illustrating an example of detecting or not detecting a gas leak from a potential gas leak source, according to some embodiments of the present invention. An indicator of a survey area (also sometimes referred to as a "field of view") is intended as an indication of how well the measurement process surveys the area around the path 74 traveled by the vehicle 24 that carries a GPS device, a mobile gas measurement device, and wind measurement device. The survey area indicator is designed such that if a potential gas leak source is located in the survey area and has a rate of leakage meeting a minimum leak rate condition, then an estimated probability of detection of a gas leak from the potential gas leak source at one or more measurement points P along the path 74 satisfies a probability condition.

Whether or not a potential gas leak source of a given strength is detectable by a gas measurement device of a given sensitivity depends on the separation distance of the source from the gas measurement device and on whether the wind is sufficient to transport gas from the gas leak source to the gas measurement device at some point along the path 74. In some embodiments, a physical model is employed that relates the measured gas concentration peak at the location of the vehicle 24 (in ppm, for example) to the emission rate of the potential gas leak source (in g/see, for example) and the distance between the source and the detection point.

There are multiple possible models that describe the propagation of a gas leak as a plume through the atmosphere. One well-validated physical model for a plume (Gifford, F. A., 1959. "Statistical properties of a fluctuating plume dispersion model". Adv. Geophys, 6, 117-137) is to model the plume as a Gaussian distribution in the spatial dimensions transverse to the wind direction. For a ground level source, the concentration c (x, y, z) at a distance x downwind, y crosswind, and at a height z from a gas leak source of strength Q located on the ground is given by Equation (1):

$$C(x, y, z) = \frac{Q}{\pi v \sigma_y \sigma_z} e^{-y^2/2\sigma_y^2 - z^2/2\sigma_z^2} \quad (1)$$

where v is the speed of the wind, and the plume dispersion half-widths $\sigma_y$ and $\sigma_z$ depend on x via functions that are empirically determined for various atmospheric stability conditions.

If we consider the plume center, where y=z=0, the concentration at the center is given by Equation (2):

$$C_{peak} = \frac{Q}{\pi v \sigma_y \sigma_z} \quad (2)$$

The dimensions of the Gaussian distribution horizontally and vertically, half-widths $\sigma_y$ and $\sigma_z$, increase with increasing distance from the source. The amount they increase can be estimated from measurements of wind speed, solar irradiation, ground albedo, humidity, and terrain and obstacles, all of which influence the turbulent mixing of the atmosphere. However, if one is willing to tolerate somewhat more uncertainty in the distance estimation, the turbulent mixing of the atmosphere can be estimated simply from the wind speed, the time of day, and the degree of cloudiness, all of which are parameters that are available either on the vehicle 24 or from public weather databases in real time. Using these available data, estimates of the Gaussian width parameters can be estimated using the Pasquill-Gifford-Turner turbulence typing scheme (Turner, D. B. (1970). "Workbook of atmospheric dispersion estimates," US Department of Health, Education, and Welfare, National Center for Air Pollution Control), or modified versions of this scheme.

For a given sensitivity of the gas measurement device, there is a minimum concentration which may be detected. Given a gas leak source of strength greater than or equal to the minimum concentration, the source will be detected if it is closer than an estimated maximum distance $X_{max}$, where this is the distance such that $\sigma_y\sigma_z=Q/(\pi vc)$. If the wind is blowing gas directly from the gas leak source to the gas measurement device, the estimated maximum distance $X_{max}$ is the distance beyond which the source may be missed. This estimated maximum detection distance may depend upon atmospheric stability conditions as well as wind speed. The formula diverges to infinity when the wind speed is very small, so it is advisable to set a lower limit (e.g., 0.5 m/s) for this quantity.

The minimum leak rate $Q_{min}$ is determined by the requirements of the application. For natural gas distribution systems, a minimum leak rate of 0.5 scfh (standard cubic feet per hour) may be used; below this level, the leak may be considered unimportant. Other minimum leaks rates (e.g. 0.1 scfh, 1 scfh, or other values within or outside this range) may be used for natural gas or other leak detection applications. The minimum detection limit of the plume $C_{min}$ is given either by the gas detection instrument technology itself, or by the spatial variability of methane in the atmosphere when leaks are not present. A typical value for $C_{min}$ is 30 ppb (parts-per-billion) above the background level (typically 1,800 ppb). Given these two values for $Q_{min}$ and $C_{min}$, and by predicting $\sigma_y$ and $\sigma_z$ given atmospheric measurements (or with specific assumptions about the state of the atmosphere, such as the stability class), one may then determine the estimated maximum detection distance $X_{max}$ by determining the value for $X_{max}$ that satisfies the following equality, Equation (3):

$$C_{min} = \frac{Q_{min}}{\pi v \sigma_y \sigma_z}. \quad (3)$$

In some embodiments the relationship between $\sigma_y$ and $\sigma_z$ and $X_{max}$ is provided by a functional relationship, a lookup table, or similar method. Because $\sigma_y$ and $\sigma_z$ are monotonically increasing functions of $X_{max}$, a unique value can be determined from this process. For example, one useful functional form is a simple power law, where the coefficients a, b, c, and d depend on atmospheric conditions: $\sigma_y=ax^b$; $\sigma_z=cx^d$.

In some embodiments, the concentration C measured close to the ground of a Gaussian plume due to a gas leak source on the ground depends on the rate of emission Q of the source, the distance x between the source and the gas measurement device, and the speed of the wind blowing from the source to the gas measurement device, in accordance with an expression of the form (Equation 4):

$$C_{min} = \frac{Q}{\pi v \sigma_y(x)\sigma_z(x)}, \quad (4)$$

The expressions for $\sigma_y$ (x) and $\sigma_z$ (x) depend on the stability class of the atmosphere at the time of measurement. In some embodiments, the stability class of the atmosphere is inferred from the answers to a set of questions given to the operator, or from instruments of the vehicle, or from data received from public weather databases. As shown in the table of FIG. 11, coefficients A, B, C, D, E and F may depend on surface wind speed and atmospheric conditions such as day or night, incoming solar radiation, and cloud cover. Mathematical forms for $\sigma_y$ (x) and $\sigma_z$ (x) are documented in Section 1.1.5 of the User's Guide for Industrial Source Complex (ISC3), Dispersion Models Vol. 2 (US Environmental Protection Agency document EPA-454/B955-003b September 1995). Given the sensitivity of the gas measurement device and the rate of emission of the smallest potential gas leak source of interest, equation (4) may be solved to find the estimated maximum distance $X_{max}$ beyond which a potential gas leak source may be missed by the gas measurement device.

Figure 9:
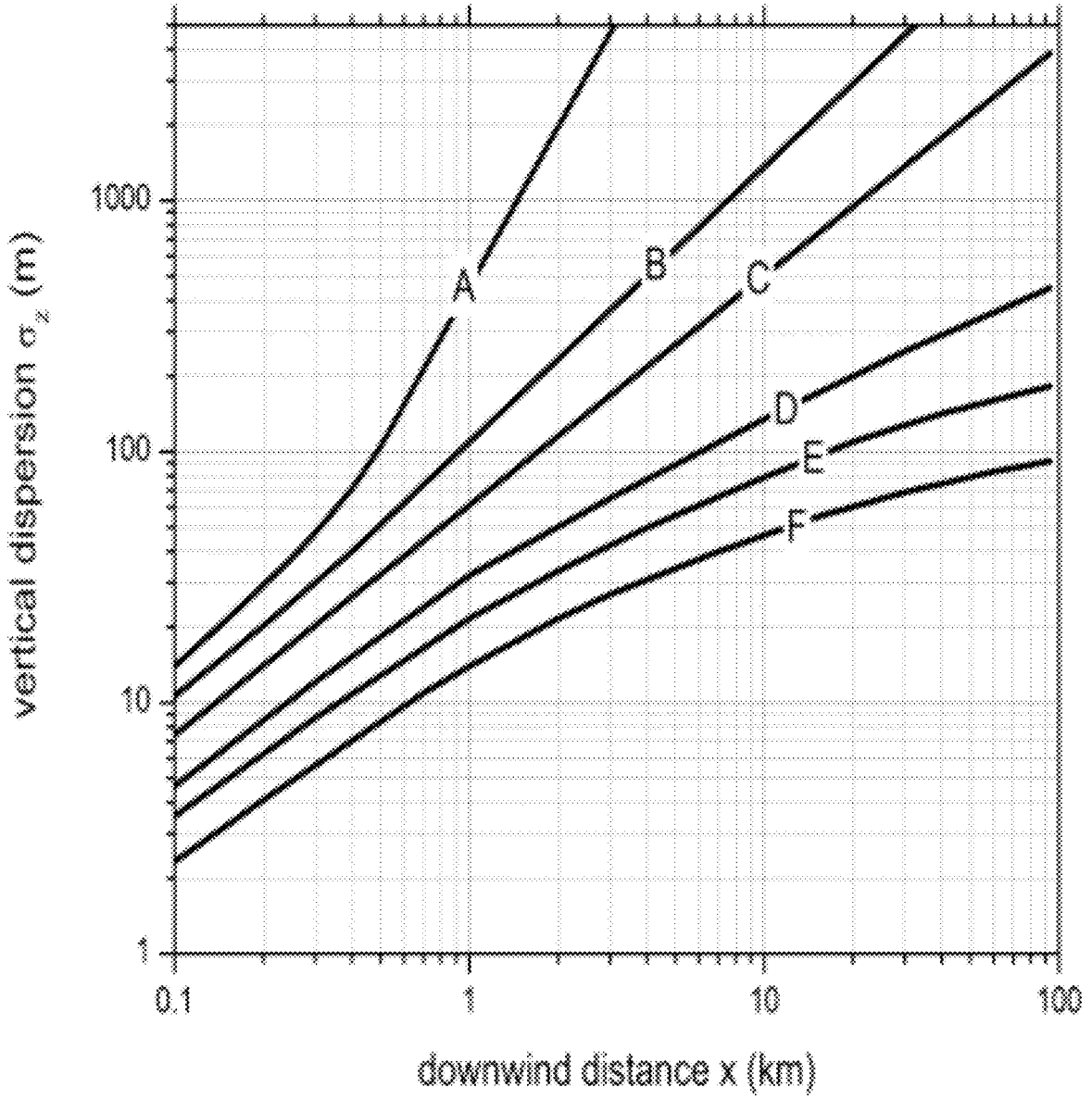
FIG. 9 is a graph of vertical dispersion coefficients of a gas plume as a function of downwind distance from a gas leak source according to some embodiments of the present invention.
Figure 10:
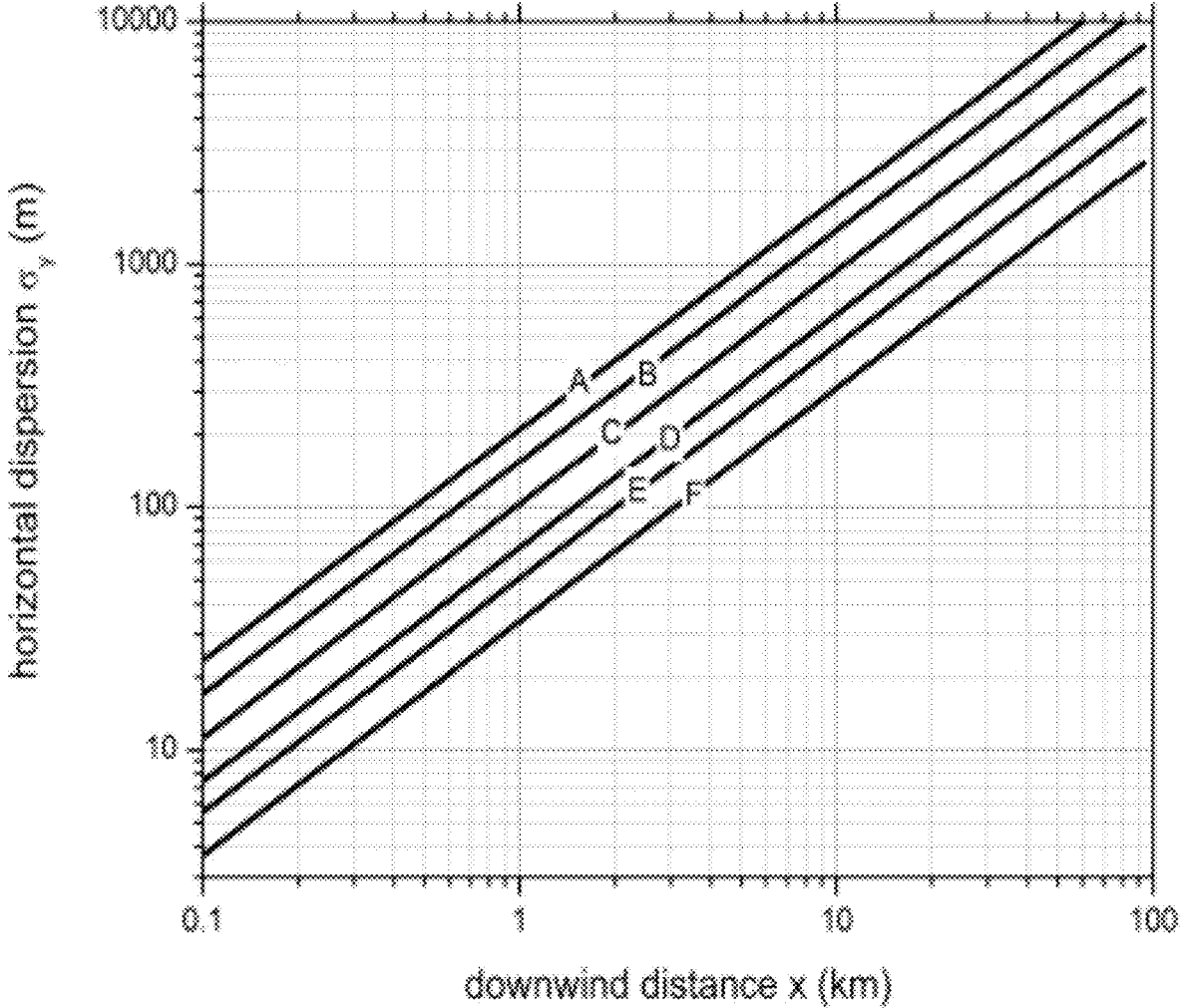
FIG. 10 is a graph of crosswind dispersion coefficients of a gas plume as a function of downwind distance from a gas leak source according to some embodiments of the present invention.

FIG. 9 is a graph of vertical $\sigma_y$ (x) dispersion coefficients of a gas plume as a function of downwind distance from a gas leak source according to some embodiments of the present invention. FIG. 10 is a graph of crosswind $\sigma_z$ (x) dispersion coefficients of a gas plume as a function of downwind distance from a gas leak source according to some embodiments of the present invention. The graphs are from de Nevers, 2000, Air Pollution Control Engineering, The McGraw-Hill Companies, Inc. The dispersion coefficients are functions of downwind distance x. In this example, dispersion coefficients are calculated based on atmospheric stability. The table of FIG. 11 gives the atmospheric stability class as a function of wind speed, day or night, cloud cover, and solar radiation. In some embodiments, the dispersion coefficients and/or the estimated maximum distance $X_{max}$ may depend upon an urban or rural environment for the gas concentration measurements and plume dispersion. For example, the estimated maximum distance $X_{max}$ may be less in an urban environment with buildings or other structures than in a rural environment.

The actual distance at which a gas leak source may be detected is reduced if there is some variability or uncertainty in the direction of the wind. This is because there is a probability that the wind blows gas in a direction such that it does not intercept the path 74 of the vehicle 24 (FIG. 6). In practice this uncertainty is usually larger than the intrinsic angular uncertainty $\sigma_y/x$ implied by the Gaussian plume model. In order to determine the effective survey area of the mobile gas measurement device, assume for this example that the wind speed remains approximately constant within a time interval –T<t<T bounding the time t=0 at which the vehicle 24 passes through a particular point P on the path 74, but that the wind direction (angle) is distributed as a Gaussian with a known mean and standard deviation.

As shown in FIG. 6, we consider the line 110 through measurement point P pointing toward the direction of the mean wind, and whether a candidate point Q on this line qualifies to be within the boundary of the survey area (i.e., within the field of view of the mobile gas measurement device of the vehicle 24). We also consider drawing a sample from the distribution of wind directions and drawing a line through the candidate point Q in this direction. If this line intersects the path 74 of the vehicle 24 within the time interval –T<t<T, and the distance from the candidate point Q to the point of intersection with the path 74 is less than or equal to the estimated maximum distance $X_{max}$, then this is regarded as detectable by the mobile gas measurement device since the potential gas leak source at the candidate point Q would have been detected along the path 74. The quantity T sets the time interval during which it is expected to detect the gas coming from the candidate point Q at measurement point P. Theoretically, the time interval can be large, but it may not be reasonable to assume that the wind statistics remain unchanged for an extended period of time. In some embodiments, the wind direction measurements are taken during a time interval less than or equal to about 2 minutes, during which time interval a gas concentration is measured at the gas concentration measurement point P. More preferably, the time interval is in the range of 10 to 20 seconds.

Figure 7:
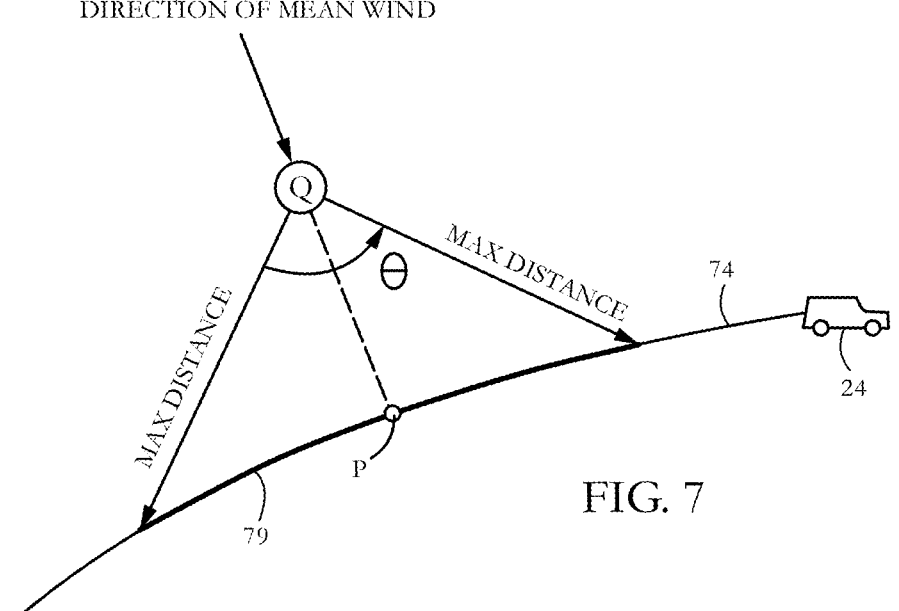
FIG. 7 is a schematic diagram of wind direction and a path of a mobile gas measurement device used to estimate a probability of detection of a gas leak from a potential gas leak source at one or more measurement points along the path according to some embodiments of the present invention.

FIG. 7 is a schematic diagram showing the estimation of a probability of detection at the measurement point P of a gas leak from a potential gas leak source at the candidate point Q, according to some embodiments of the present invention.

The probability of detection at measurement point P is estimated according to an angle θ subtended by a segment 79 of the path 74 relative to the candidate point Q for the potential gas leak source. The path segment 79 is positioned within a distance of the candidate point Q that is less than or equal to the estimated maximum distance $X_{max}$. The probability of detection is preferably estimated according to a cumulative probability of wind directions with respect to the subtended angle θ. The cumulative probability of wind directions may be determined according to a representative wind direction (e.g., a mean, median, or mode of the wind direction measurements) and a wind direction variability (e.g., variance or standard deviation) calculated from the wind direction measurements.

The candidate point Q is deemed to be within the boundary of the survey area if the probability of successful detection of a potential gas leak source at the candidate point Q, over the distribution of wind directions, satisfies a probability condition. In some embodiments, the probability condition to be satisfied is an estimated probability of successful detection greater than or equal to a threshold value, typically set at 70%. In general, as the candidate point Q is moved a farther distance from the gas concentration measurement point P, the range of successful angles becomes smaller and the probability of success decreases, reaching a probability threshold at the boundary of the territory deemed to be within the survey area.

Figure 8:
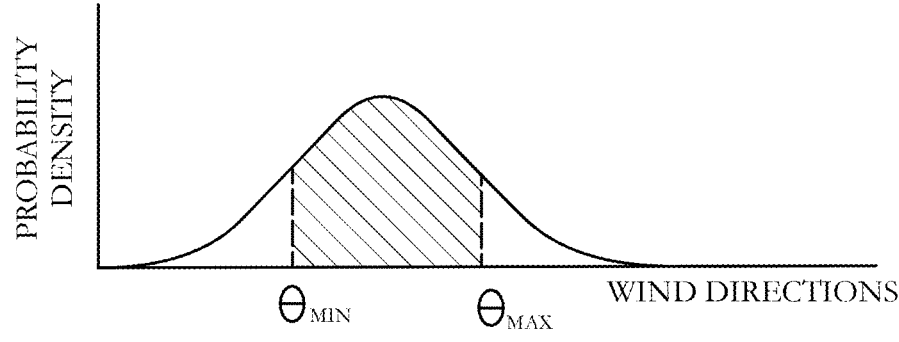
FIG. 8 is a graph of probability density vs. wind directions for estimating a probability of detection of a gas leak from a potential gas leak source according to some embodiments of the present invention.

FIG. 8 is a graph of probability density vs. wind directions for estimating a probability of detection of a gas leak from a potential gas leak source, according to some embodiments of the present invention. The area under the curve spans a range of possible angles θ for the successful detection of a potential gas leak from a candidate point. The probability density is preferably generated as a Gaussian or similar distribution from the calculated mean and standard deviation of the wind direction measurements in the area of the gas concentration measurement point P, FIG. 7. If the angle θ subtended by the path segment 79 relative to the candidate point Q encompasses a percentage of possible wind vectors that is greater than equal to a threshold percentage (e.g., 70%, although the percentage may be adjusted to other values such as 50%, 60%, 67%, 75%, 80%, or 90% in some embodiments), and if the distance from the candidate point Q to the measurement point P is less than the estimated maximum distance $X_{max}$, then the candidate point Q is deemed to be within the survey area.

The above process is repeated as different measurement points along the path 74 are chosen and different candidate points are evaluated for the probability of successful detection of a potential gas leak source. The cumulative distribution of the wind direction function together with a root finding algorithm are useful for efficiently determining the boundary of the survey area. For example, referring again to FIG. 7, the root finding algorithm may consider candidate points along the line of mean wind direction starting at the estimated maximum distance $X_{max}$ from measurement point P, and iteratively (e.g. using a bisection or other method) moving closer to the measurement point P along the mean wind direction line until the angle θ subtended by the path segment 79 is sufficient to meet the probability threshold, as determined from the cumulative probability of wind directions over the subtended angle θ, FIG. 11. Referring again to FIG. 4, the survey area indicator 80 may be displayed on the map 70 as a colored "swath" adjoining the path 74 and extending in a substantially upwind direction from the path. Quantifying Emissions In some embodiments, a sequence of measurements and associated analyses as described herein are used to track emission rates over time. The description below focuses primarily on identifying and characterizing natural gas leaks in an under- and above-ground transmission and distribution system, but the exemplary sequential analysis approaches described below may be applied to other systems in which understanding heterogeneous ground level emissions is useful. The end user of such a system may be an individual interested in gas leak detection and emissions quantification.

The ability to quantify the emissions rate of fugitive natural gas leaks on a distribution or transmission system is potentially useful to the industry in several ways. For example, the emission rate of a given leak (or leaking segment of pipeline) may be one factor affecting the hazard posed by the leak. Under certain circumstances, leaks with larger emissions rates may result in a high probability of gas migrating into a confined space, thereby presenting an explosion hazard. Additionally, when not burned, methane is a potent greenhouse gas (GHG). Gas utilities are interested in surveying their transmission and distribution systems to quantifying the emissions rates of individual leak and pipe segments so as to decide how to direct limited resources to repair and upgrade their systems to achieve maximal benefit in terms of improved safety and reduced GHG emissions.

Beyond the ability to quantify fugitive emissions rates at a given moment in time, the ability to track changes in the emissions rates of leaks or pipe segments also provides useful information. For example, slow trends in emissions rates may be used to identify and track the progression of leaks caused by corrosion. In some systems, especially those with significant amounts of old cast-iron pipes, fugitive leaks can either appear abruptly, or have a sudden and large increase in emissions rates as a result of acute outside forces damage, such as that caused by frost heave as the frozen ground swells and dislodges a pipe or joint. In some cities in the northeastern United States, frost-heave is responsible for dozens of catastrophic distribution integrity failures each winter. Measurements collected with methane sensors mounted on vehicles provide the ability to rapidly and repeatedly survey a distribution pipeline network to identify new leaks and mitigate the hazard they present as soon as possible after they occur.

Measuring the emission rate(s) of a leak is a challenging task. Direct methods, such as those where the concentration is measured inside a large bag or tent that attempts to capture over all the emission points, or those that require excavation, are time- and cost-intensive and may be impractical for surveying large distribution networks. Mobile methods that measure the downwind concentration of methane in a gas plume at one or more vertical locations can be used to estimate the emission rate. At the same time, the single-measurement precision of such methods can be noisy, with the best achievable precision being governed by the stochastic behavior of plume propagation in a locally-divergent turbulent atmosphere.

The emission rates of individual leaks may vary due to factors that don't represent changes in the severity of the damage to pipe. One such factor is pipeline pressure: for a given size hole in a pipe, the leak rate will vary directly with the pressure in the pipe. Furthermore, the rate at which gas escapes into the atmosphere may exhibit variability due to, e.g., changes in surface permeability driven by diurnal or seasonal temperature changes, by the moisture content of the soil, and/or by other factors.

Exemplary systems/methods described herein may automatically account for such inherent sources of variability occurring on a similar time scale as the interval between measurements, and allow calculation of a probability or confidence level with which a given measurement or group of measurements represents a change in emissions rate indicative of a possible change in the state of health of a leaking pipe.

In some embodiments, changes in the emission rate of a gas emission source are detected by performing sequential, time-series measurements of gas concentrations away from the source. The emission rate, or another quantity that is a statistical proxy for emission rate, of the gas emission source is measured for each of a plurality of measurement runs performed along the same or similar paths. In some embodiments, the measurement runs use a survey protocol that minimizes variability (noise) in the measurement due to factors such as the distance between the leak at the measurement location. The survey protocol may include driving the same lanes of the street at the same time of day on each subsequent round of measurements. A graphical user interface may be used to receive user input indicative of the geospatial location (e.g. identity of a current lane) of the vehicle at particular times, and to provide an operator with indicators of a recommended choice of lane at a current geospatial location, and/or indicators of real times associated with the current geospatial location during one or more prior measurement runs.

In post-acquisition data processing, different measurements are grouped together when determined to be likely to have originated from the same source. Such grouping allows associating each of the measurements with a given source. The measured emission rates or measured values of a statistical proxy are corrected to account for variability in the measurement caused by changes in conditions between measurements. The probability that a significant change in emissions rate occurred between any two groups of measurements that are sequential in time is quantified. An output is then generated that reports whether a change occurred, and, if a change did occur, at what time or within which range of times the change occurred, and a measure of the probability or statistical confidence that the change occurred.

In some embodiments, the measurements are taken onboard a moving vehicle recording geospatial position and time and primary gas concentration measured at one or more vertical measurement locations. The emission rate quantification technique may incorporate a gas flux chamber (an enclosure made of plastic or other impervious material placed over a suspected leak location) combined with a gas concentration detection apparatus. The emission rate quantification technique may also incorporate a tracer release method whereby tracer gas of known concentration is released at a known rate in close spatial proximity to an emission source with a different chemical composition than the tracer gas and having an unknown emission rate; the dispersion of the tracer gas concentration may be quantified to calculate the unknown emission rate of the source of interest from concentration measurements of the source gas.

In some embodiments, the emission rate measurement technique incorporates a mobile flux plane as described above. In some embodiments, a peak primary concentration enhancement above an ambient background level is used as an indicator or statistical proxy for emission rate. In some embodiments, a line flux defined as the integral of the product of the concentration enhancement and wind speed lateral to the path of the vehicle with respect to the distance traveled through a cross-section of the gas plume may be used as a statistical proxy for emission rate.

In some embodiments, measurements may be clustered according to the proximity of their associated measurement locations to each other, and an estimated source position may be taken as a representative position derived from the cluster. Such a representative position may be a location determined by spatially averaging the clustered locations. Associating measurements that likely originate from the same candidate source may be performed using a geo-spatial density clustering algorithm such as DBSCAN. In some embodiments, associating measurements with a candidate source may include associating all measurements taken within a given radius of an estimated source location.

In some embodiments, correcting the measured emission rates or values of the statistical proxy is accomplished using an atmospheric transport model and measurements of one or more of wind speed, air temperature, cloud cover fraction, cloud height, longwave radiation, shortwave radiation, ground surface temperature, or conductive heat flux through the ground. In some embodiments, correcting the measured emission rates or values of the statistical proxy is accomplished by normalizing the measured values by the average value of the emission rates or statistical proxy values measured for a set measurements made for one or more other sources in a window of time around which the measurement for the source interest is made. In some embodiments, correcting the measured emission rates or values of the statistical proxy is accomplished according to an empirically-determined relationship between the expectation value of the emission rates or values of the statistical proxy for a given source strength, measured wind speed, and range of possible downwind distances between the source and measurement locations.

In some embodiments, at least four measurements are available. The statistical test to be applied may be a Komolgorov-Smirnov test applied between groups of measurements that are sequential in time with each subset consisting of at least two measurements. Performing such a comparison may include comparing all possible combinations of two subsets of sequential measurements, each containing at least two sequential measurements. In some embodiments, subsets of measurements may be binned by wind direction, and statistical change analysis is performed independently on each of the binned subsets. The statistical test to be applied may make use of theoretical or empirically-estimated probability distributions of emission rate or emission-rate proxy over a range of leak rates, distances from the source, and measurement conditions combined with a prior probability distribution of leak rates. In some embodiments, a significant change may be determined to have occurred if the p-value of the statistical test for at least one pair of measurement sets being tested meets a threshold condition. In particular, a significant change may be determined to have occurred between the pair of measurement subsets with the smallest p-value that meets the threshold condition. The probability that a change occurred may be calculated using the same p-value, which represents that probability that the two measurement subsets were drawn from different underlying distributions. The time at which the change occurred may be defined by the earliest time range separating two subsets whose output of the statistical test meets the threshold condition.

Exemplary change-detection methods described below attempt to address the large variability in measured amplitudes that may be observed even in the absence of leak rate changes. Large variations in measured amplitudes for a fixed leak rate may be due a number of factors, including variability in atmospheric conditions, and local spatial variations in plume concentrations. In some instances, localized amplitudes detected from an unchanged leak source at similar locations were observed to vary by as much as a factor of ten between different measurement runs. Identifying leak rate changes can be particularly challenging in the context of such large variations between different measurement runs performed for an unchanging leak.

In some embodiments, identifying a change in emission rate may include quantifying an emission rate before and after a time boundary, and comparing the change in the emission rate estimates across the time boundary to a predetermined threshold. Such an approach may effectively use the mean and standard deviations of the two measurement value distributions. The measurement values may include amplitudes, values of flux, or values of statistical proxies for flux and/or amplitude such as amplitude or line integral results computed as described below. Such an approach may be particularly effective in the presence of relatively low variations in detected amplitudes between different measurement runs in the absence of emission rate changes, and/or if relatively high numbers (e.g. tens or hundreds) of measurement data points are available for a given emission source. Under such conditions, the intra-collection variabilities (e.g. the standard deviations or error bars of the measurements) may be lower than the inter-collection distances (e.g. differences between the means or other representative values). In other words, such an approach may work well if the error bars for the two collections of measurement values do not overlap substantially.

Figure 12:
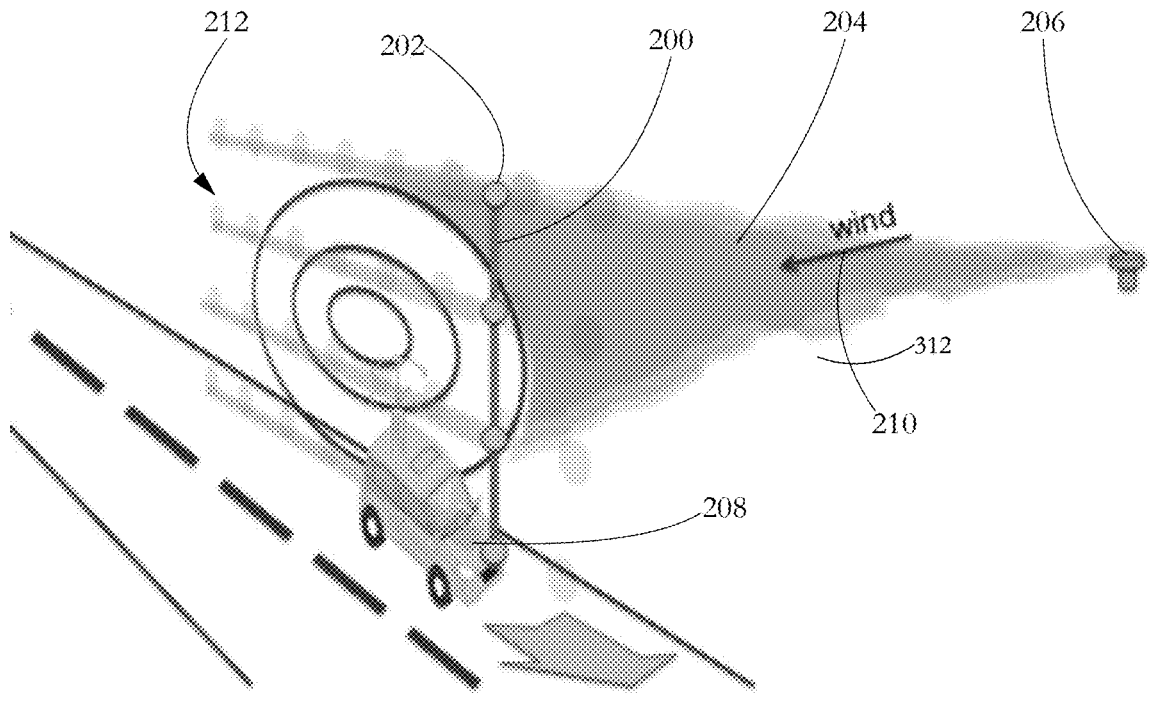
FIG. 12 illustrates an exemplary geometry of a 2-D integral used to estimate a flux of methane passing through a 2-D surface swept out by a collection mast according to some embodiments of the present invention.

FIG. 12 illustrates schematically a vertical mast 200 which includes multiple vertically-spaced inlet (measurement) ports 202, each sampling concentration independently and each corresponding to a measurement channel. In a single-inlet configuration, a single active inlet port is used to collect data. The mast is attached to a vehicle as described above, and driven through a gas plume originating at gas emission source. In some embodiments, the arrangement of the measurement ports can be changed using a servo system to toggle between two or more pre-determined measurement port configurations, or to a configuration where one or more of the measurement ports moves dynamically during a measurement run. In some embodiments, a configuration of measurement ports can include vertically separated measurement ports and one or more additional low-height measurement ports near ground level that can be used specifically to identify on-road below-the-vehicle leaks that are not sufficiently offset from the vehicle's axis of motion. In some embodiments, each of a plurality of inlets may be coupled to a dedicated corresponding spectrometer as described above. In some embodiments, a common spectrometer may be fluidically coupled to multiple inlet ports through a system including valves and long tubes forming gas storage chambers; in such a system, gas collected through multiple ports may be collected in parallel into corresponding gas storage chambers, and then released serially into the spectrometer to provide a delayed playback of the gas collection process.

Consider a method of sampling methane concentration using multiple inlets 202 arranged vertically on a mast 200 which is driven through a downwind transect of a gas plume 204 originating at a localized source 206, as illustrated in FIG. 12. Measurements of instantaneous wind speed and direction are made simultaneously using a wind sensor mounted onto a vehicle 208. The prevailing wind direction during the sampling period is shown at 210.

A flux-plane technique may be used to determine an estimate the flux of methane passing through a two-dimensional surface 212 swept out by the mast 200 according to $$Q = \int_A k(C(x,y) - C_0)\overrightarrow{u(x,y)} \cdot \hat{n} \, dA \qquad (5)$$

wherein C(x, y) is the concentration at a given point in space on the surface A (shown at 212 in FIG. 12), $C_0$ is the background concentration of the target gas, $\overrightarrow{u(x,y)}$ is the velocity of the gas, and $\hat{n}$ is the normal to the surface element dA. The constant k may be used to convert volumetric flow in $m^3/s$ to moles/s, such that the unit of emission rate Q is, for example, moles/second. A flux computed according to eq. (5) provides an indicator of the corresponding emission rate, and may be substantially equal to the emission rate if the entire gas plume is captured by the swept surface. Eq. (5) implies that the transect is made at an instant in time, an assumption that is generally valid so long as the transect is performed at a driving speed that is fast compared to the component of wind speed normal to the two-dimensional surface. In some embodiments, it was found that the single-measurement precision of such a technique is limited by the nature of plume propagation in the atmosphere. Due to local divergence of the turbulence field, an individual measurement can result in emissions rate estimates that vary upward or downward from the true value by a factor of 2 to 3 or more, depending on the specific conditions of the measurement.

In some embodiments, the downwind concentration enhancement may be measured at a single vertical measurement location, for example using a mast having a single active inlet. The concentration enhancement may be measured as peak height above the ambient background level, or as a line flux according to $$F = \int_{x1}^{x2} k(C(x) - C_0)\overrightarrow{u(x)} \cdot \hat{z} \, dx \qquad (6)$$

where F is the line flux, $\hat{z}$ is the horizontal unit vector perpendicular to the direction of travel, and the range of integration $x1 < x < x2$ is sufficiently large so as to cover the full extent of the plume transect. The line flux may be used as an indicator of the corresponding emission rate. The line flux of eq. (6) can be expected to be proportional to the 2-D flux of eq. (5). In some embodiments, the constant k may be chosen so that, on average, a result of using eq. (6) for a single-inlet system matches a 2-D flux computed using eq. (5) for a multi-inlet system using a mast. In an exemplary implementation, we found that a suitable value for k may be between 1 and 2 square meters, for example about 1.5 square meters.

In some embodiments, measurements of peak amplitude or line flux (eq. (6)) were observed to tend to exhibit larger single-measurement variability for a given fixed leak rate compared to those made with a flux plane (eq. (5)). In the case of amplitude-based measurements, the spread of single-measurement values can, however, be misleading as a metric of comparison to the flux-plane technique. In particular, the single-inlet technique can be particularly useful if P(a|Q), the function describing the probability of observing an amplitude a given a leak emissions rate Q, follows a log-normal distribution:

$$P(a \mid Q) = \frac{1}{a\sigma\sqrt{2\pi}} e^{\frac{-(\ln a - \mu)^2}{2\sigma^2}} \qquad (7)$$

which is a function of the amplitude a where exp(σ), the geometric standard deviation, is a constant, and where exp(μ) is the geometric mean of the distribution, where μ=μ(Q) is a logarithmic function of Q.

In some embodiments, an approximate flow rate of a natural gas leak Q is calculated from the integrated product of the measured methane concentration c(x) (in units of mass per volume) multiplied by the lateral wind speed $u_{lat}(x)$ perpendicular to the vehicle.

$$Q = L \int_{x_s}^{x_e} c(x) u_{lat}(x) dx \qquad (8)$$

where $x_s$ and $x_e$ are the plume start and end locations, and L is a length scale which corresponds to the anticipated vertical dispersion of the plume. L may be determined empirically from controlled release experiments, as described in US Patent Publication No. 2015/0047416 A1, published Feb. 19, 2015, entitled "Scanned 1-D Gas Plume Profile and Flux Measurements Using Multiple Analysis Measurements," which is incorporated herein by reference. In some embodiments, a lower detection limit for leak flow rate estimation may be estimated to be about 0.1 SCFH, and flow rate estimates for leaks below this level are deemed to be unreliable. Such a value may be used as a quality control threshold. Equation (8) expresses the observation that, for a given set of measured concentrations, the corresponding leak flow rate is expected to be higher if the survey vehicle passed through the plume in a direction perpendicular to the wind, since the survey sampled a relatively small extent of the plume, and lower if the survey vehicle passed through the plume along or counter to the wind, since the survey samples a larger extent of the plume.

In some embodiments, the likelihood that a leak is a natural gas leak is determined according to a determined relationship between co-measured ethane and methane levels as represented for example by an ethane/methane ratio. In some embodiments, a Picarro P3300 Surveyor gas analyzer measures methane ($CH_4$), ethane ($C_2H_6$) and water vapor ($H_2O$) concurrently. The ethane to methane concentration ratio of the gas mixture measured during a Surveyor plume detection can be used to differentiate a natural gas source from a biogenic methane source (e.g. sewer or landfill gas). Although natural gas primarily consists of methane (>90% $CH_4$) trace amounts of other gasses are also present in the supply. The existence of ethane in a Surveyor plume measurement sample is often a good indication that the gas originated from a natural gas facility, while the absence of ethane in the mixture is an indication that the source of the plume is biogenic. The methane and ethane content of a natural gas supply depends on the geologic source of the gas, and the mixture of gas from various sources. Therefore, the ethane content in the natural gas is variable and quantified in terms of the ethane to methane ratio. Regular measurements of the natural gas composition from various locations may be made and used for source attribution.

In some embodiments, multiple measurements of methane and ethane concentration during a plume detection are used to calculate the distribution of ethane/methane ratio values for each indication. The distribution of ethane/methane ratios is compared with a threshold value provided for a given location to determine if the measured plume contained natural gas, biogenic gas or a mixture of both types. The concentration ratio distribution may be used to provide a confidence interval for the reported disposition, for example, 90% confidence that a particular indication is natural gas. Indications that are determined to be biogenic gas with a predetermined confidence interval (e.g. >90%) are flagged and excluded according to the quality control procedure.

In some embodiments, indicators other than ethane may be used to determine whether a particular methane detection is due to natural gas. Such indicators may include, for example, one or more concentrations of odorants found specific to natural gas, one or more isotope ratios (e.g. 13C/12C methane, 2H/1H methane), or non-detection of traces associated with other methane sources (e.g. carbon monoxide, ethylene, acetylene, other species emitted from mobile combustion sources).

In some embodiments, a probability that a leak was detected on a given set of measurement runs is determined by the number of times an indication was generated divided by the number of opportunities there were to generate an indication. The number of opportunities to generate an indication may be calculated as the number of times the vehicle passed within a given distance (e.g. 20 meters) of the geometrical center of the aggregated leak indications.

In some embodiments, an estimated distance to a leak source may be determined using (a) spatial-scale analysis of the plume detections within a cluster, and/or more coarsely, as (b) the relative distance between indications in a cluster. Indications generated from leaks far away from the vehicle are subject to varying wind conditions that cause them to be detected broadly along the vehicle path. Indications that are detected close together are more likely attributed to a nearby source. In this case, one parameter that can be used as a proxy for distance to the leak source is the median pairwise distance of all of the leak indications in the cluster.

Since it may be difficult to isolate a single leaking component using only vehicle-based measurements, it may be advantageous to consider the characteristics of nearby gas distribution infrastructure. For example, any distribution infrastructure within a certain distance (e.g. 200 feet) of the aggregated leak indications may be considered as a potential location of the leaking source. The leak indications can then be associated with attributes including component type (e.g. transmission main, distribution main, service line, connection, valve, regulator) as well as information about the individual component (e.g. material, age, size, repair history).

Emissions Assessment Over Time in a Target Area

Natural gas distribution network operators may wish to assess the state of their networks and associated emissions/leaks in a given area during particular reporting periods, such as one or more months, quarters or years. The systems/methods described below facilitate such assessment.

Cumulative methane emissions in a target area during a reporting period generally depend on at least three factors: the number of leaks open in a network during the period of reporting, the flow rate of each of the leaks, and the duration the leaks remain open. The large sizes of common natural gas networks (several thousands to hundreds of thousands of miles of main) often require vehicle-mounted mobile systems able to rapidly cover large areas.

Exemplary end-to-end measurement and calculation procedures as described herein facilitate reliable assessments of cumulative methane emissions in a given area, and provide associated uncertainty analyses. Described procedures include, among others, defining the specification of the problem to solve including the gas network and the reporting period to cover, and collecting and processing information including emission and uncertainty data to generate an auditable assessment of the amount of methane released in the atmosphere by the gas network over the reporting period. A probabilistic approach allows scaling the calculation to large networks without necessarily investigating every gas indication.

Figure 13:
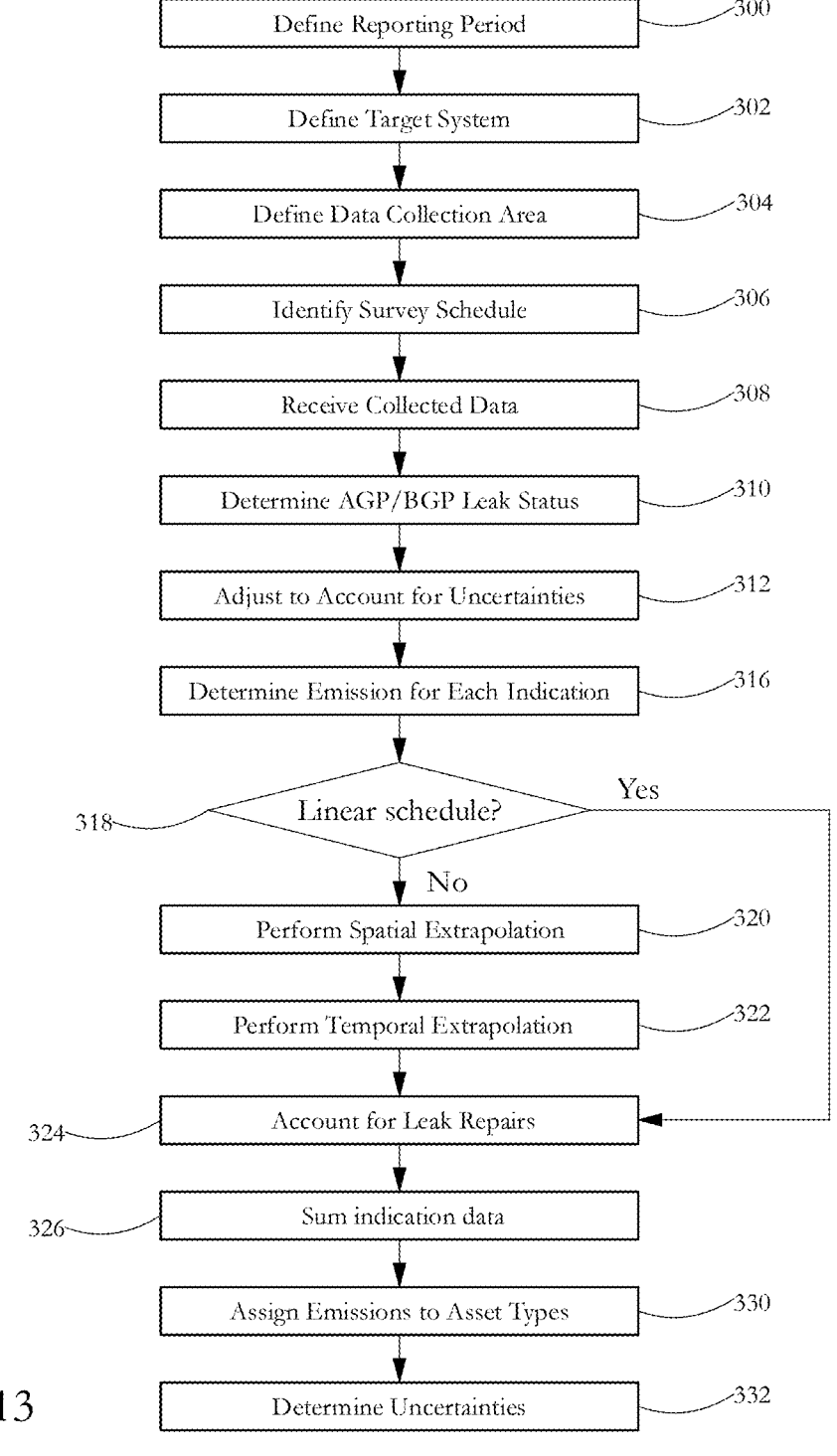
FIG. 13 illustrates an exemplary process for determining emissions and associated uncertainties for a target area over a reporting period, according to some embodiments of the present invention.

FIG. 13 shows an exemplary sequence of steps performed in an area- and time-based assessment of natural gas distribution infrastructure leaks according to some embodiments. In particular, the assessment includes determining a quantity of total methane emitted in a target area over a reporting period according to measurements performed at various discrete times over at least parts of the reporting period.

In a step 300, a reporting period is defined according to user input and/or predetermined values. For example, the reporting period may be defined by a start date and end date, and/or start date and duration. Exemplary reporting periods include one or more years, months, weeks and/or days. A common reporting period is a full or partial calendar year (e.g. 2024, year-to-date). In a step 302, a target or system area is defined according to user input and/or predetermined data. Defining the target area may comprise identifying, directly or indirectly, a list of transmission network assets (e.g. pipelines, services such as meters, etc.) covered by the emission reporting. The list of assets may be identified directly, e.g. by assembling a list of the assets, and/or indirectly, e.g. by identifying a spatial area that includes/identifies the assets. Defining the target area may also include identifying a number of area properties/metadata, such as mileage of mains and services, number of services, and other associated data. For example, in some embodiments, services may be converted to pipeline mileage using an average service length in order to generate an equivalent total pipeline mileage for the area.

In a step 304, a data collection area is defined. The data collection area includes any subpart or the entirety of the system/target area that is surveyed at least once during the reporting period. If the data collection area is smaller than the entire system/target area, a spatial extrapolation step may be performed as described below. Preferably, the data collection area is representative of the entire system/target area, so that spatial extrapolation produces accurate results. A data collection area may be deemed representative according to whether multiple factors are representative, including mix of area types (urban, sub-urban, commercial, industrial, and rural), mix of pipeline materials (steel—protected/non-protected, cast iron, plastic, etc.), mix of pipeline vintages, especially if a specific material/vintage may impact emissions, and mix of leak survey and repair frequencies. The number of leaks on a segment directly depends on the time since the last survey and possible repair. The data collection area preferably includes a mix of leak survey frequencies that properly represents the full system/target area.

In a step 306, a survey schedule for the data collection area is identified. In some embodiments, the survey schedule includes a time-stamped list of subareas surveyed on different dates, and associated metadata such the share of system/target assets surveyed per unit of time. Preferably, the survey schedule reflects a linear or quasi-linear increase in system/target assets surveyed over the reporting period (i.e. constant or quasi-constant rate of assets surveyed per unit time). If the survey schedule is deemed non-linear, a non-linearity adjustment may be performed as described below. Substantial non-linearity may occur for example if surveying is disproportionately performed early or late during the reporting period.

In a step 308, geospatially-referenced survey data is received and/or collected as described above. Preferably, data collection is performed using a predetermined protocol designed to ensure consistency of survey conditions. In an exemplary embodiment, four to six passes are performed in late evening or early morning for each area of interest. Leak indications may or not be more closely investigated on each pass. The field of view is recorded in each pass, and is used to assess the parts and/or percentage of the data collection area that is not surveyed by each pass, and/or collectively by the multiple passes of a daily collection set.

In a step 310, each indication is classified as a likely above-ground (AGP) or below-ground (BGP) indication. The classification may be probabilistic, i.e. each indication is assigned a probability that it is above-ground and/or below-ground. The classification allows network operators to selectively assess below-ground leaks, which are of particular interest for prioritizing repairs. In some embodiments, the probability may be assigned according to a model fitted on many indications investigated by different utilities. Using a broad range of utilities reduces the impact of specific leak detection practices and allows the use of a large enough data set for a statistically valid representation. In some embodiments, each indication's measured flow rate is reduced by a factor equal to its BGP or AGP. For leaks confirmed through an on-site investigation, the BGP or AGP may be forced to 1.0, as appropriate.

Figure 14:
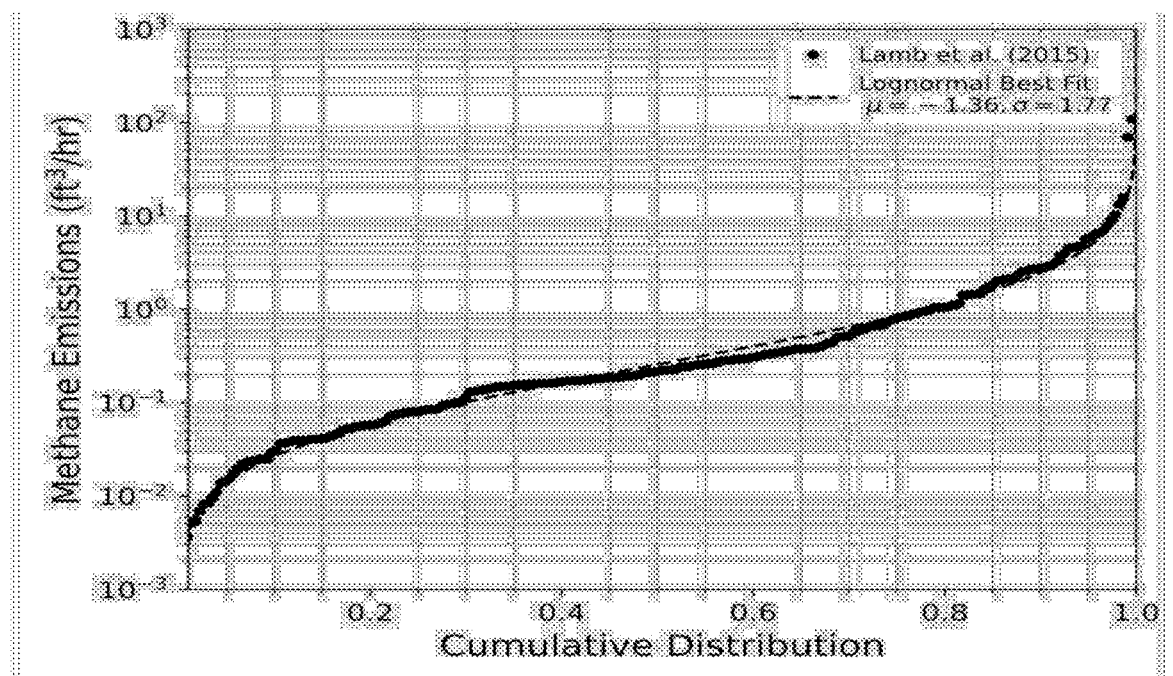
FIG. 14 illustrates an exemplary log-normal distribution of methane emissions according to some embodiments of the present invention.

In a step 312, leak emission size data are adjusted to account for uncertainties in the underlying data. Common leak size distributions are highly-skewed, with a small number of larger leaks accounting for most emissions. FIG. 14 shows a graph of methane emissions (in cubic ft per hour) as a function of cumulative distribution, as reported in MacMullin, Sean and Rongère, François-Xavier, "Measurement-Based Emissions Assessment and Reduction Through Accelerated Detection and Repair of Large Leaks in a Gas Distribution Network," available at SSRN: https://ssrn.com/abstract=4229362, Jan. 12, 2023. In some embodiments, measured emissions are adjusted according to a prior probability distribution that is representative of the actual leak size distribution of the system. Experimentally, a lognormal distribution was observed to be generally acceptable. Table 1 below lists a number of observed distributions that may be used to adjust measured emission data:

TABLE 1

| Prior Reference | Observed Distribution | Recommended Log Normal Distribution | Mean [SCFH] | Median [SCFH] |
|---|---|---|---|---|
| α | No leaks are greater than 10 SCFH and about 15% are between 1 SCFH and 10 SCFH | $\mu = -2.0$ $\sigma = 1.77$ | 0.65 | 0.14 |
| β | Less than 5% of leaks are greater than 10 SCFH and about 20% are between 1 SCFH and 10 SCFH | $\mu = -1.36$ $\sigma = 1.77$ | 1.30 | 0.26 |
| γ | 5% to 7.5% of leaks are greater than 10 SCFH and about 25% are between 1 SCFH and 10 SCFH | $\mu = -0.9$ $\sigma = 1.77$ | 1.95 | 0.4 |
| δ | 5% to 10% of leaks are greater than 10 SCFH and about 30% are between 1 SCFH and 10 SCFH | $\mu = -0.5$ $\sigma = 1.77$ | 2.91 | 0.61 |

TABLE 1-continued

| Prior Reference | Observed Distribution | Recommended Log Normal Distribution | Mean [SCFH] | Median [SCFH] |
|---|---|---|---|---|
| ε | 10% to 15% of leaks are greater than 10 SCFH and about 35% are between 1 SCFH and 10 SCFH | $\mu = 0$ $\sigma = 1.77$ | 4.79 | 1.00 |

In some embodiments, each detection is placed in one of four order-of-magnitude bins according to the detection's measured flow rate. Each detection is then assigned a representative flow rate (RFR) calculated using the data of Table 1.

TABLE 2

| Bin [SCFH] | Representative Flow Rate (RFR) for each Prior Reference [SCFH] | | | | |
|---|---|---|---|---|---|
| | α | β | γ | δ | ε |
| $B_1$ (≥10) | 7.1 | 9.7 | 12.3 | 15.0 | 19.4 |
| $B_0$ [1, 10[ | 1.7 | 2.2 | 2.7 | 3.2 | 4.1 |
| $B_{-1}$ [0.1, 1[ | 0.4 | 0.5 | 0.7 | 0.8 | 1.0 |
| $B_{-2}$ (<0.1) | 0.1 | 0.1 | 0.2 | 0.2 | 0.2 |

In a step 316, an emission quantity or rate is determined for each indication, and in a step 326 the individual indication emissions are summed to generate an emission quantity for the target area as described below. A step 318 determines whether the survey schedule meets a linearity condition, i.e. is determined to be linear or quasi-linear. If the schedule is deemed linear, the emission for each indication is determined according to the relation:

$$E_i = RFR_i \cdot BGP_i \cdot (\text{Min(End,Repair)} - \text{Start}) \qquad (9)$$

where End is the end of the reporting period, Start is the start of the reporting period. Eq. (9) takes a representative flow rate (RFR), scales it by the probability that it is due to a below-ground leak and further multiplies it by the time period commencing at the start of the reporting period and ending either at the end of the reporting period or at a time of repair of the respective leak (if applicable). Thus, eq. (9) accounts for leak repairs (step 324). The total emission is then calculated as the sum of the emissions for individual indications (step 326), and the steps 320-322 described below need not be performed.

In some embodiments, if the survey schedule defined in step 318 is deemed non-linear, a more complex calculation is performed, including by performing spatial and/or temporal extrapolations as described below with reference to steps 320-322. In a step 320, spatial extrapolation is performed in order to estimate emissions from assets that have not been surveyed. Assets that have not been surveyed can be classified as belonging to gaps in field-of-view coverage, i.e. assets that are close to the survey path but downwind or otherwise not deemed surveyed ($\text{Miles}_{Gap}$ below), or belonging to areas remote from the survey path ($\text{Miles}_{Out}$ below). $\text{Miles}_{Gap}$ is generally relatively small, and $\text{Miles}_{Out}$ is generally relatively larger. Extrapolation may employ the expectation that the leak density (number of leaks per mile of main) and the average flow rate associated with leaks are the same in non-covered areas as in the covered areas. In a step 322, temporal extrapolation is performed in order to account for emissions during time periods outside a survey window defined by the start and end of data collection.

In some embodiments, the total emissions for the system and the reporting period are determined according to the relation:

$$E = \sum_i^{N_i} RFR_i \cdot BGP_i \cdot (\text{Min(End, Repair)} - \text{Start}) + \tag{10}$$

$$\frac{Miles_{Gap} + Miles_{Out}}{Miles_{Surveyed}} \cdot \sum_i^{N_i} RFR_i \cdot BGP_i \cdot (\text{End} - \text{Start})$$

In some embodiments, the Miles ratio in the right-hand term may be replaced by other ratios representing the extent of the relevant infrastructure not surveyed (in the numerator) and the extent of the relevant infrastructure surveyed (in the denominator). Pipeline length is merely one (convenient) measure of infrastructure extent surveyed or not surveyed.

As discussed above with reference to eq. (9), eq. (10) accounts for leak repairs through its left-hand term. The right-hand term of eq. (10) includes a spatial- and temporal-extrapolation term that accounts for non-surveyed areas (through the fraction of miles non-surveyed to miles surveyed), and performs temporal extrapolation at least implicitly by considering emissions during the entire reporting period (End-Start), even if some leaks might started emissions after the start of the reporting period. Eq. (10) relies on the observation that two sources of error generally offset each other: first, some leaks start before they are detected, and second, some leaks occur after their area has been surveyed. The form of eq. (10) considers all leaks to have started at the start of the reporting period (Start), even though some may have started later. This overestimate compensates for the fact that some leaks may start late in the process and not be detected by the survey, and thus would not be explicitly included in the emission data summed according to eq. (10).

As noted above, eqs. (9) and (10) account for gas leak repairs (step 324) through the variable Repair. Gas operators repair leaks as there are detected, either through surveys (compliance surveys or special surveys) and through odor calls that, in general, are independent of the vehicle-based data collection process described herein. Such repairs follow a repair schedule that is generally based on a system of prioritization based on the hazard associated with each leak. The table below provides an example of a policy:

TABLE 3

| Leak grade | Repair time frame | Share of total leaks |
|---|---|---|
| 1 | Immediate | 20% |
| 2 | 1 year | 30% |
| 3 | 3 years | 50% |

The impact of repairs on reported emissions is two-fold, depending on whether repairs occurred before or after survey times, and the two impacts balance each other if data collection and repairs are performed linearly through the year. First, late repairs reduce the time the leaks are open, leading to lower emissions post-repair. Second, early repairs reduce the leaks detected through the data collection process, since some of the repairs may have happened before the respective area is surveyed, but after the start of the reporting period. As discussed below in further detail, if data collection and repairs are performed at a constant pace across the year, the two impacts exactly compensate each other:

$$\text{Repair}_{reduction} = \overline{RFR_l} \cdot N_{rep} \cdot \frac{Y}{2} \tag{11a}$$

$$\text{Emissions}^{Addition} = \overline{RFR_i} \cdot Y \cdot \frac{N_{rep}}{2} \tag{11b}$$

where Y denotes the reporting period (e.g. one year), and $N_{rep}$ denotes number of repairs.

In a step 330, emissions may be assigned by asset type. The asset type may be defined as a material type and/or structural type. In some embodiments, each indication is proportionally assigned to different assets in its vicinity as described below. If a leak has been confirmed through on-site investigation, its BGP is set to 1.0 the leaks is fully assigned to its correct asset type.

In a step 332, a number of uncertainties and/or confidence intervals are determined as described below. Methane emissions over a reporting period depend on the number of leaks in the system, corresponding leak flow rates, and the duration the leaks stay open during the reporting period. The total emissions may be expressed as $$\text{Emissions} = \int_{t_0}^{t_f} \sum_{i=1}^n q_i(t) \cdot dt \tag{12}$$

Where $q_i(t)$ is the leak flow rate of the ith leak.

Consider a log-normal distribution of leak flow rates, as illustrated in FIG. 14, characterized by an expected (mean) value $\mu$ and standard deviation $\sigma$ of the function's logarithm. The confidence interval can be estimated using the Cox formula:

$$q \in \left[ \exp\left( \mu + \frac{\sigma^2}{2} - z\sqrt{\frac{\sigma^2}{k} + \frac{\sigma^4}{2(k-1)}} \right), \tag{13} \right.$$

$$\left. \exp\left( \mu + \frac{\sigma^2}{2} + z\sqrt{\frac{\sigma^2}{k} + \frac{\sigma^4}{2(k-1)}} \right) \right]$$

where k is the size of the sample and z is the z-score corresponding to the confidence interval.

If the leak density variability is random, it follows a Poisson distribution, with a confidence interval is provided by the $\chi^2$ function:

$$n \in \left[ \frac{\chi^2\left(\frac{\alpha}{2}, 2 \cdot k\right)}{2}, \frac{\chi^2\left(1 - \frac{\alpha}{2}, 2 \cdot (k+1)\right)}{2} \right] \tag{14}$$

Another source of uncertainty is measurement technique. Using controlled and field tests, an exemplary uncertainty of a system expressed on the logarithm of the flow rate was determined to follow a normal distribution with parameters $\mu=0$, $\sigma=0.95$. This measurement uncertainty may be integrated in calculations to avoid bias due to the skewness of leak size distribution generally observed in distribution systems. Bayesian inference may be used to assign correct flow rates for the different bins assigned to leaks. Such an approach reduces bias, and converges toward a unique solution independently of the precision of the measurement techniques. Remaining errors are random noise characterized by the variance in the measurements. The resulting uncertainty of the average flow rate can be assessed using the confidence on an unknown mean for measurements characterized by their standard deviation:

$$\bar{q} \in \left[ \bar{q}_m \cdot \left(1 - z \cdot \frac{\sigma}{\sqrt{n}}\right), \ \bar{q}_m \cdot \left(1 + z \cdot \frac{\sigma}{\sqrt{n}}\right) \right] \tag{15}$$

where n is the number of measurements and z is the z-score corresponding to the confidence interval.

In some embodiments, an overall uncertainty is determined by considering the independent sources of uncertainty described above. The measurement uncertainty for a given sample may be convoluted with the sampling uncertainty to obtain the average flow rate uncertainty based on the measurement of a sample:

$$\bar{q}_A(\bar{q}_m) = \bar{q}_A[\bar{q}_S(\bar{q}_m)] \tag{16}$$

where $\bar{q}_A$ is the actual average flowrate, $\bar{q}_S$ is the average flowrate on the sample, $\bar{q}_m$ is the measured average flow rate on the sample.

The flow rate uncertainty may be combined with the leak density uncertainty through a product function, since emissions are:

$$\text{Emissions} = \int_{t_0}^{t_f} \sum_{i=1}^{n} q_i(t) \cdot dt = \int_{t_0}^{t_f} \sum_{k=1}^{p} \overline{n_k}(t) \cdot l_k \cdot \overline{q_k} \cdot dt \tag{17}$$

where $\overline{n_k}(t)$ is the leak density per unit of length of the system for the population of leaks having the same average flow rate $\overline{q_k}$, and $l_k$ is the length of the system for the population k. The combined uncertainty may be evaluated for example via a Monte Carlo simulation.

The reasoning underlying eqs. (9-10) above may be better understood by considering suitable survey schedules in production environments of energy and/or natural gas distribution companies. In a large territory, leak surveys may be yearlong activities. The number of found leaks is therefore not necessarily equal to the total number of leaks open during the year, since for example some leaks may appear in an area after it has been surveyed. If the leaks appear randomly and linearly over time, the number of leaks as a function of time may be modeled as:

$$\tilde{n}_i^j(t) = n_i^{0,j} + \lambda_i^j \cdot (t - t_0) \tag{18}$$

If the leak surveys are performed continuously over the year, then the rate/frequency of survey w for an area j at a time t may be expressed as $$w^j(t) = \frac{A^j}{Y} = \text{Const.} \tag{19}$$

where: j is the index of the area for which the emissions are to be calculated; i is the index of the material and type of pipe corresponding to different leak flow rate, which may be removed when considering a unique emission factor across materials and asset types; $t_0$ is the starting time of the reporting period for which the emissions will be calculated;

$$\tilde{n}_i^j(t)$$

is the number of open leaks in the system for the material and asset i at the time t (the ~ indicates that the number is calculated without repair); $r_i(t)$ is the flow rate of the open leaks of the system for the material i at the time $$t; \lambda_i^j$$

is the rate of apparition of new leaks in the are a j for the material and asset i; $w^j(t)$ is the rate of survey at the time t in the area j; $A^j$ is the total area of the area j; Y is the duration of the reporting period (e.g. one year).

The emissions for the surveyed area $A^j$ over a reporting period Y may be expressed as:

$$E^j{}_{t_0}^{t_f} = \int_{t_0}^{t_f} \sum_i \tilde{n}_i^j(t) \cdot r_i(t) \cdot dt \tag{20}$$

where $r_i(t)$ is the flow rate of the open leaks of the system for the material i at the time t. If the leak flow rate is constant, eq. (20) may be expressed as:

$$E^j{}_{t_0}^{t_f} = \sum_i r_i \cdot \int_{t_0}^{t_f} \tilde{n}_i^j(t) \cdot dt \tag{21}$$

Replacing $$\tilde{n}_i^j(t)$$

by the expression of eq. (18) yields:

$$E^j{}_{t_0}^{t_f} = \sum_i r_i \cdot \int_{t_0}^{t_f} n_i^{0,j} + \lambda_i^j \cdot (t - t_0) \cdot dt = \sum_i r_i \cdot \left( n_i^{0,j} \cdot Y + \lambda_i^j \cdot \frac{Y}{2} \cdot Y \right) \tag{22}$$

Figure 15:
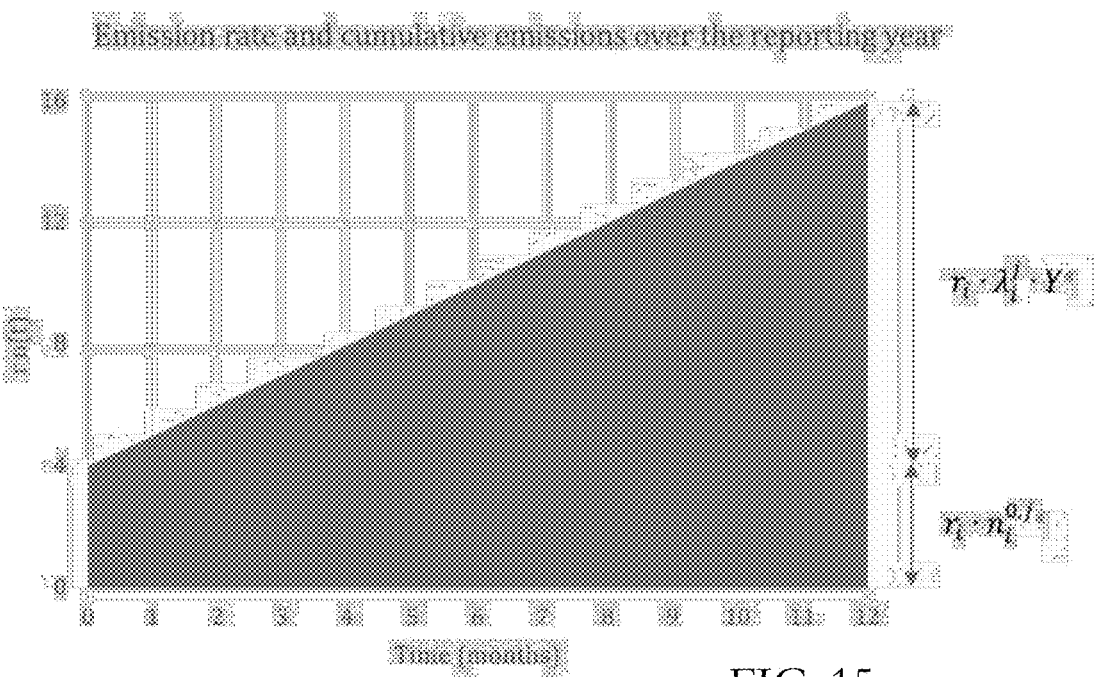
FIG. 15 illustrates an exemplary linear progression of cumulative emissions over time, according to some embodiments of the present invention.

FIG. 15 shows an exemplary linear progression of cumulative emissions over time, represented as the area to the right/below the line.

The number of leaks found over a small time increment may be expressed as:

$$df_i^j = \frac{w^j(t)}{A^j} \cdot dt \cdot \tilde{n}_i^j(t) = \frac{n_i^{0,j} + \lambda_i^j \cdot (t - t_0)}{Y} \cdot dt \tag{23}$$

Then, the number of found leaks over the reporting year is:

$$f_i^j = \int_{t_0}^{t_0+Y} \frac{n_i^{0,j} + \lambda_i^j \cdot (t - t_0)}{Y} \cdot dt = n_i^{0,j} + \lambda_i^j \cdot \frac{Y}{2} \tag{24}$$

The emissions are then:

$$E^j{}_{t_0}^{t_f} = \sum_i r_i \cdot f_i^j \cdot Y \tag{25}$$

Figure 16:
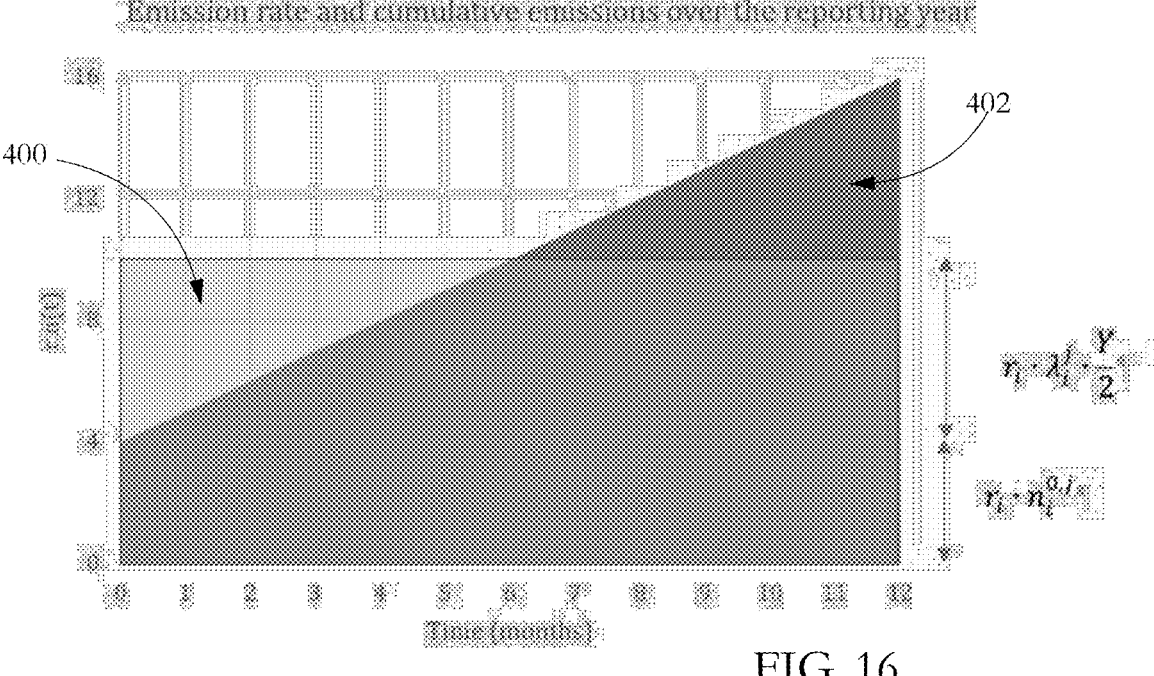
FIG. 16 shows cumulative emissions over the reporting period for leaks considered opened since the beginning of the reporting period, overlaid on the linear progression of FIG. 15, for a linear survey schedule, according to some embodiments of the present invention.

FIG. 16 shows cumulative emissions over the reporting period for leaks considered opened since the beginning of the reporting period, overlaid on the linear progression of FIG. 15. As shown, if the survey is performed continuously at a constant pace over the reporting year, cumulative emissions are equal to the emissions of the found leaks considered opened since the beginning of the year. The overestimation due to new leaks that appeared during the year of interest but are deemed open since the beginning of the year, illustrated at 400 in FIG. 16, is exactly compensated by the underestimation due to leaks appearing after survey, illustrated at 402 in FIG. 16.

Consider a hypothetical survey performed continuously over a year (the reporting period), that sweeps west-to-east over the target area over the year so that the westernmost side is surveyed in January and the easternmost side in December. Furthermore, consider the emission quantification approach described above, in which any encountered leak is deemed to have started emitting at the beginning of the year. Summing emissions in this way undercounts emissions on the west side, because the survey misses late-arising leaks, and overcounts emissions on the east side, because the survey deems all east-side leaks, even late-arising ones, to have started emitting at the beginning of the year. The overcount and undercount compensate each other.

In such an approach, the number of found leaks includes leaks that appeared before the beginning of the reporting period. For such leaks, the emissions are correctly computed by considering them open since the beginning of the reporting period (e.g. a year). For a low-frequency survey, for example a five-year compliance survey, the number of pre-existing leaks is much greater than the number of new leaks appeared in the year. For a five-year survey, the number of leaks may be expressed as:

$$n_i^{0,j} = 4 \cdot \lambda_i^j \cdot Y \qquad (26)$$

If the survey is not performed continuously at a constant pace over the reporting year, a correction can be calculated by comparing the actual number of leaks found over the time and the linear function defined above:

$$f_i^j = \int_{t_0}^{t_0+Y} \frac{w^j(t)}{A^j} \cdot \left(n_i^{0,j} + \lambda_i^j \cdot (t - t_0)\right) \cdot dt = \qquad (27)$$

$$n_i^{0,j} + \int_{t_0}^{t_0+Y} \frac{w^j(t)}{A^j} \cdot \left(\lambda_i^j \cdot (t - t_0)\right) \cdot dt$$

For example, if the survey is only performed during the fourth quarter and at constant pace:

$$\frac{w^j(t)}{A^j} = 0 \; t \in \left[0; \frac{3 \cdot Y}{4}\right] \qquad (28a)$$

$$\frac{w^j(t)}{A^j} = \frac{4}{Y} \; t \in \left[\frac{3 \cdot Y}{4}; Y\right] \qquad (28b)$$

$$n_i^{0,j} + \int_{t_0}^{t_0+Y} \frac{w^j(t)}{A^j} \cdot \left(\lambda_i^j \cdot (t - t_0)\right) \cdot dt = \qquad (28c)$$

$$n_i^{0,j} + \frac{4 \cdot \lambda_i^j}{Y}\left[\frac{Y^2}{2} - \frac{9 \cdot Y^2}{32}\right] = n_i^{0,j} + \frac{7 \cdot \lambda_i^j}{8} \cdot y$$

Figure 17:
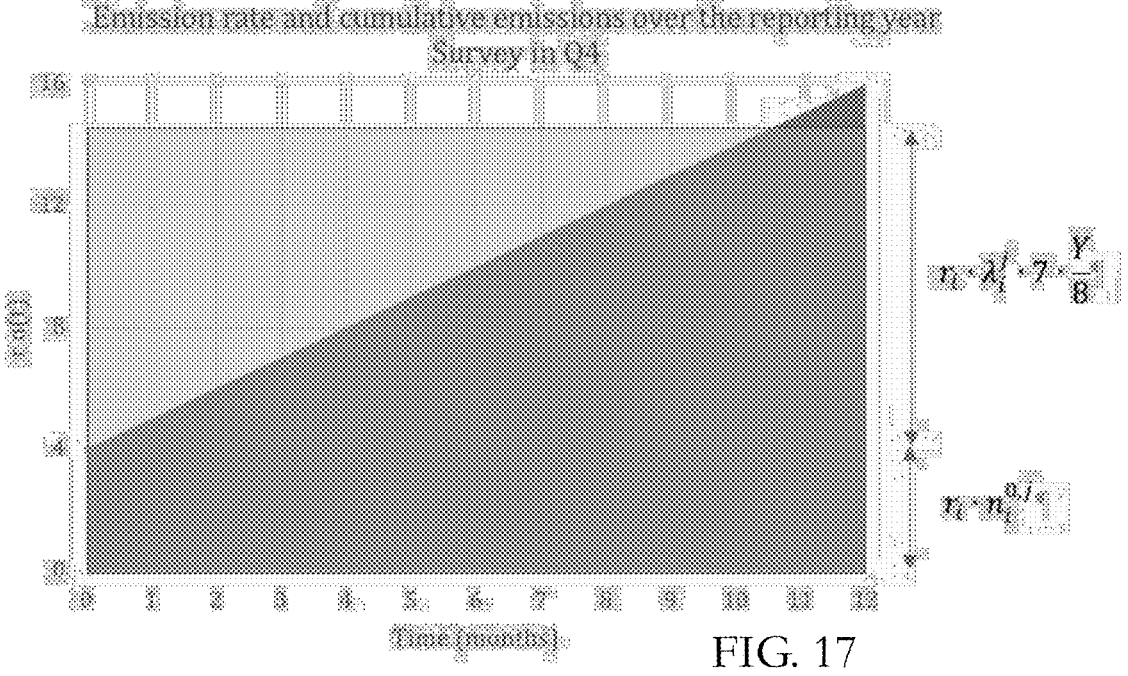
FIG. 17 shows cumulative emissions over the reporting period for leaks considered opened since the beginning of the reporting period, overlaid on the linear progression of FIG. 15, for a delayed survey schedule, according to some embodiments of the present invention.

FIG. 17 shows cumulative emissions over the reporting period for leaks considered opened since the beginning of the reporting period, overlaid on the linear progression of FIG. 15. By correcting the area from the underestimated and overestimated triangles, we can calculate the emissions as:

$$E^j = \sum_i r_i \cdot \left(n_i^{0,j} \cdot T + (f_i^j - n_i^{0,j}) \cdot \left(1 - \frac{45}{112}\right) \cdot Y\right) \qquad (29)$$

where $$f_i^j$$

is number of leaks found during the survey, and $$n_i^{0,j}$$

is the number of original leaks appearing since/before the beginning of the year. The original number of leaks is determined by the survey frequency, and may be determined from the number of found leaks by considering the leak appearance to be linear. For example, for a 5-year survey cycle the number of original leaks may be set to be $$n_i^{0,j} = \frac{4}{5} \cdot f_i^j,$$

which estimates that ⅘ of the found leaks appeared in the first four years of the cycle, and the final ⅕ of the found leaks appeared in the fifth year.

Conversely, if the survey is only performed during the first quarter and at constant pace:

$$\frac{w^j(t)}{A^j} = \frac{4}{Y} \; t \in \left[0; \frac{Y}{4}\right] \qquad (30a)$$

$$\frac{w^j(t)}{A^j} = 0 \; t \in \left[\frac{Y}{4}; Y\right] \qquad (30b)$$

$$n_i^{0,j} + \int_{t_0}^{t_0+Y} \frac{w^j(t)}{A^j} \cdot \left(\lambda_i^j \cdot (t - t_0)\right) \cdot dt = n_i^{0,j} + \frac{4 \cdot \lambda_i^j}{Y}\left[\frac{Y^2}{32}\right] = n_i^{0,j} + \frac{\lambda_i^j}{8} \cdot Y \qquad (30c)$$

Figure 18:
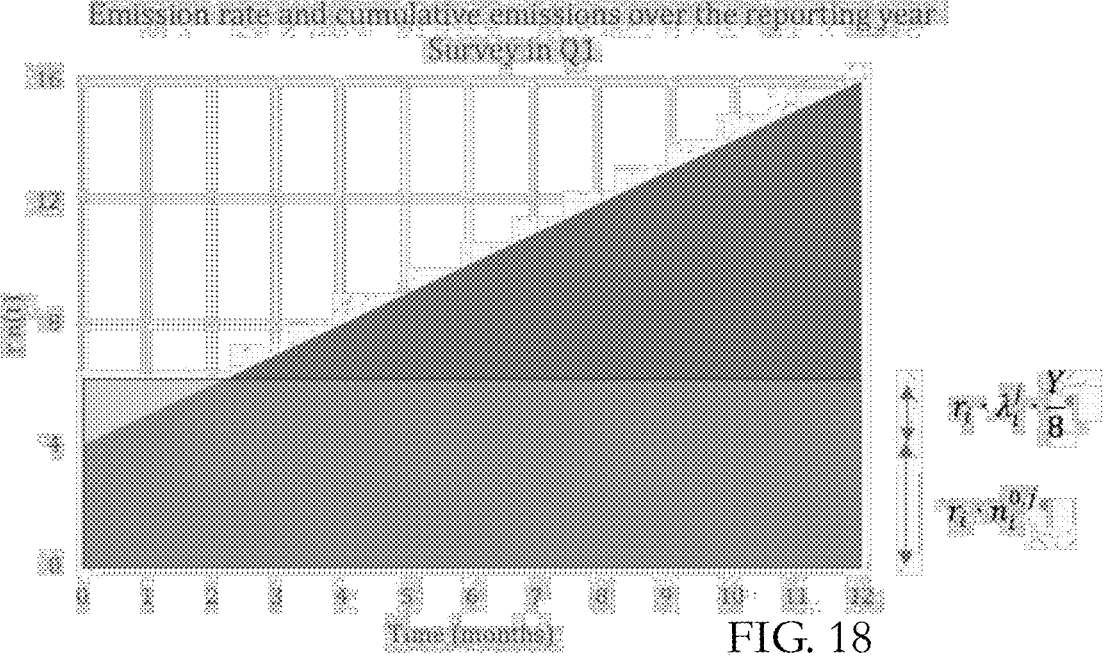
FIG. 18 shows cumulative emissions over the reporting period for leaks considered opened since the beginning of the reporting period, overlaid on the linear progression of FIG. 15, for an accelerated/early survey schedule, according to some embodiments of the present invention.

FIG. 18 shows cumulative emissions over the reporting period for leaks considered opened since the beginning of the reporting period, overlaid on the linear progression of FIG. 15. By correcting the area from the underestimated and overestimated triangles, we can calculate the emissions as:

$$E^j = \sum_i r_i \cdot \left(n_i^{0,j} \cdot Y + (f_i^j - n_i^{0,j}) \cdot \left(1 + \frac{45}{16}\right) \cdot Y\right) \qquad (31)$$

Consider now a survey schedule shown by monthly mileage, as listed below in Table 4 and illustrated graphically in FIG. 19.

TABLE 4

| Month | Mileage |
|---|---|
| 1 | 33.9 |
| 2 | 15.9 |

TABLE 4-continued

| Month | Mileage |
|---|---|
| 3 | 20.9 |
| 4 | 27.2 |
| 5 | 55.3 |
| 6 | 90.7 |
| 7 | 116.2 |
| 8 | 173.5 |
| 9 | 250.2 |
| 10 | 255.8 |
| 11 | 218.6 |
| 12 | 69.8 |

A correction factor may be calculated based on the integration of the schedule per month. For every month the number of found leaks may be calculated as:

$$f_i^j = n_i^{0,j} + \lambda_i^j \cdot \sum_{Month} \frac{w^j(month)}{A^j} \int_{t_{ini}}^{t_{end}} t \cdot dt = \tag{32}$$

$$n_i^{0,j} + \lambda_i^j \cdot \sum_{Month} \frac{w^j(month)}{A^j} \cdot \frac{t_{end}^2 - t_{ini}^2}{2} = n_i^{0,j} + 0.67 \cdot \lambda_i^j \cdot Y$$

A correction may be calculated by comparing the areas of the overestimated and underestimated triangles, as illustrated above, which yields:

$$\Delta_{Under} = \frac{(1 - 0.67)^2}{2} = 0.055 \tag{33a}$$

$$\Delta_{Over} = \frac{(0.67)^2}{2} = 0.223 \tag{33b}$$

The emissions may then be calculated as:

$$E^j = \sum_i r_i \cdot \left( n_i^{0,j} \cdot Y + \left( f_i^j - n_i^{0,j} \right) \cdot (1 + \Delta_{over} - \Delta_{Under}) \cdot Y \right) = \tag{34}$$

$$\sum_i r_i \cdot f_i^j \cdot \left( \frac{n_i^{0,j}}{f_i^j} \cdot Y + \left( 1 - \frac{n_i^{0,j}}{f_i^j} \right) \cdot 0.83 \cdot Y \right)$$

As noted above, leaks may be estimated to occur linearly, which yields:

$$\frac{n_i^{0,j}}{f_i^j} = \frac{p-1}{p} \tag{35}$$

where p is the survey cycle frequency expressed in reporting periods (e.g. years). As illustrated, the emissions calculated with a variable schedule may differ from the value estimated for a constant pace survey:

$$E_{cst}^j = \sum_i r_i \cdot f_i^j \cdot Y \tag{36}$$

Nonetheless, emissions may determined as described above for any survey schedule, including variable schedules.

Spatial Extrapolation Considerations, Subdividing Collection Area into Representative Areas As noted above, if all the territory of target area is not covered via survey, then a spatial extrapolation may be performed to determine the total emissions over the target area. Preferably, in order to generate accurate results, the collection area is representative of the full system, and/or divided in areas of specific characteristics that may then be extrapolated to the full territory by taking into account their share, i.e. weighting data from each collection area according to the area's share of the total. At the same time, accuracy depends on sample size, and subdividing the collection area reduces sample size. Thus, in an approach which divides the target area into multiple regions, there is a trade-off that balances the impact on accuracy of the size of the sample and the representativity of the collection area.

To perform such a division, in some embodiments a first step is to assess the representativity of the collection area for each of the four classes of characteristics described above with reference to step 304 in FIG. 13. Specifically, as noted above, a data collection area may be deemed representative according to whether multiple factors are representative, including mix of area types (urban, sub-urban, commercial, industrial, and rural), mix of pipeline materials (steel—protected/non-protected, cast iron, plastic, etc.), mix of pipeline vintages, especially if a specific material/vintage may impact emissions, and mix of leak survey and repair frequencies.

The share of area types is characterized by each area's extent of gas distribution infrastructure relative to the total extent of gas distribution infrastructure in the target area, expressed for example as number of miles of main compared to the total number of miles of main in the target area.

Figures 19, 20:
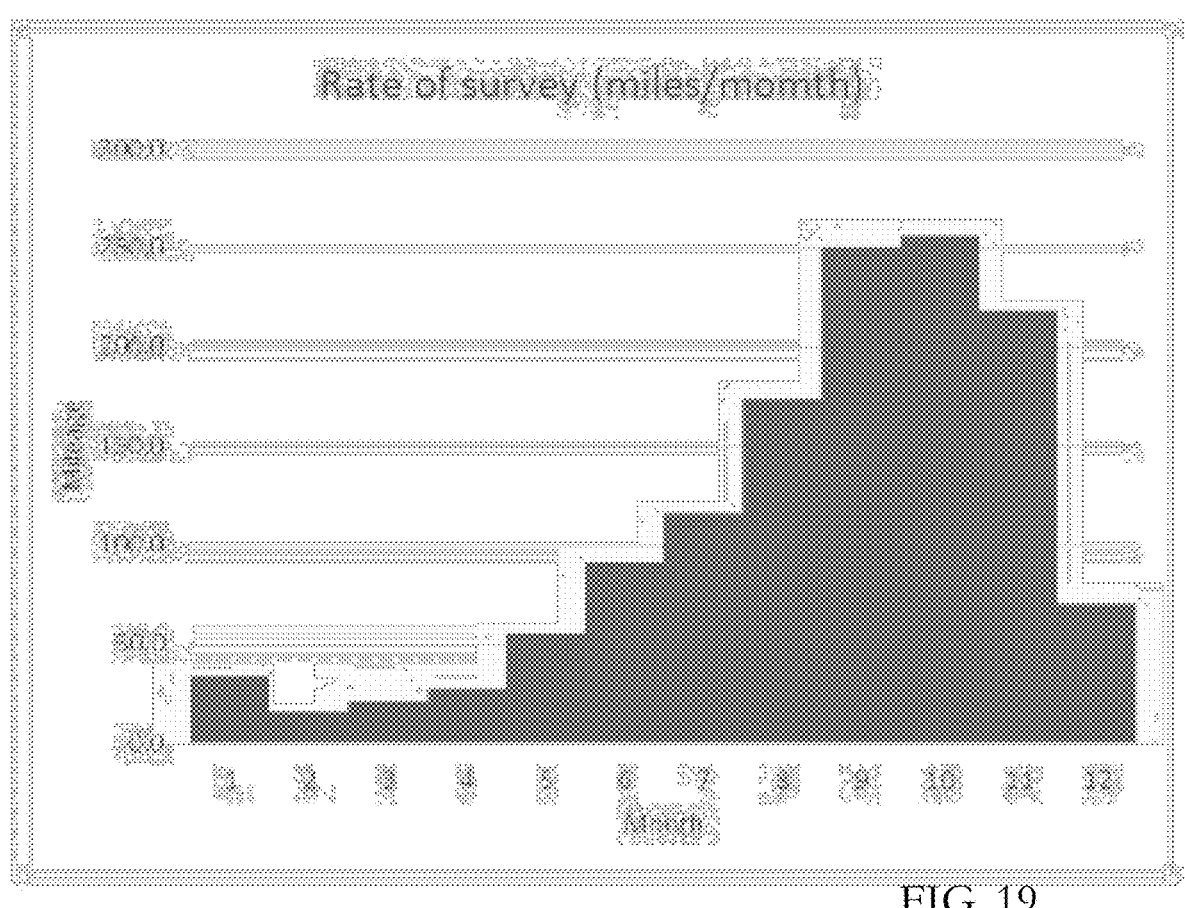
FIG. 19 illustrates an exemplary dependence of survey rate with time across a reporting period of a year, according to some embodiments of the present invention.
FIG. 20 illustrates an exemplary mismatch in characteristics between a total/system area and a corresponding data collection area according to some embodiments of the present invention.

FIG. 20 shows an exemplary comparison of the representation of different area types in a collection area and in a total system (target area), expressed in miles of main. In the illustrated example, urban, suburban and industrial areas were overrepresented while commercial and rural were underrepresented. Consider an example in which emissions per mile depend on the area type as follows:

TABLE 5

| | EF (scfh/M) |
|---|---|
| Urban | 2 |
| Suburban | 3 |
| Comm | 5 |
| Ind | 4 |
| Rural | 1 |

In some embodiments, system emissions may be calculated both directly (via measurements on the entire system), and via extrapolation of the emissions from a more limited data collection area, in order to test the robustness of extrapolation techniques. In one exemplary such analysis, the difference in this specific case was determined to be only about 1%, even in the presence of substantial differences between the shares of different area types in the data collection area and the full territory and in the emissions per mile of each area type. In some embodiments, a tentative subdivision of area types may be verified a posteriori when calculations are completed.

Emissions per mile generally depend on pipeline materials. Cast iron is generally the leakiest, followed by unprotected steel, then protected steel, then plastic (polyethylene). Certain networks may also include legacy pipeline materials such as copper and PVC. Also, there can variability within the same material category. For example, certain pipeline vintages are known to have specific characteristics, such as seventies' vintage plastic pipelines with known issues for older Aldyl-A and Drisco pipes. In addition, while the density of leaks per mile differs between materials, it has been observed that the average flow rate of a leak is independent of, or weakly dependent on, pipeline material.

In some embodiments, establishing sample sizes of different materials preferably keeps the share of materials across different vintages similar to the full system in order to support a direct extrapolation, and maintains sample sizes (number of potential leaks) large enough to assure adequate accuracy if separation is needed. The second goal can be of particular concern for leaky materials that are relatively infrequent in the system.

In some embodiments, a representativeness analysis may use three parameters: observed proportion of a category in the area of data collection (% AoC); actual proportion of a category in the full system/target area (% Syst); and impact of the category on emission (ICE), representing a ratio of emission density generally observed to the average emission density. ICE may be normalized such that its sum weighted by % Syst on each class equals 1.

In some embodiments, a deviation of an area of data collection from the system may be estimated for each category as:

$$Dev_{AoC}(\text{Category}) = \left| 1 - \frac{\%AoC}{\%Syst} \right| \cdot \%Syst \cdot \text{ICE} \tag{37}$$

As a first approximation, a category may be deemed representative if its deviation in the area of data collection compared to the full system is less than a predetermined threshold, such as 1%, 2%, 5%, or 10%. A category may be deemed partially representative if between the first threshold and another higher threshold (e.g. between 2% and 5%, or between 5% and 10%) and not representative if greater than the higher threshold (e.g. higher than 5% or 10%).

Accounting for Repairs in Emissions Calculations Over the Reporting Period

Leak repairs, which may performed linearly along a reporting period or on other schedules, affect computed emissions for the reporting period. If the number of repaired leaks over the reporting period (e.g. a year) is known, the corresponding reduction of emissions can be calculated as:

$$\text{Repair}_{reduction} = \overline{RFR_i} \cdot \int_0^Y rep(t) \cdot (Y - t) \cdot dt \tag{38}$$

If rep(t) is constant over time, i.e. repairs are performed at a constant rate, then:

$$\text{Repair}_{reduction} = \overline{RFR_i} \cdot rep \cdot \frac{Y^2}{2} = \overline{RFR_i} \cdot N_{rep} \cdot \frac{Y}{2} \tag{39}$$

where $N_{rep}$ is the number of repaired leaks per year.

Figure 21:
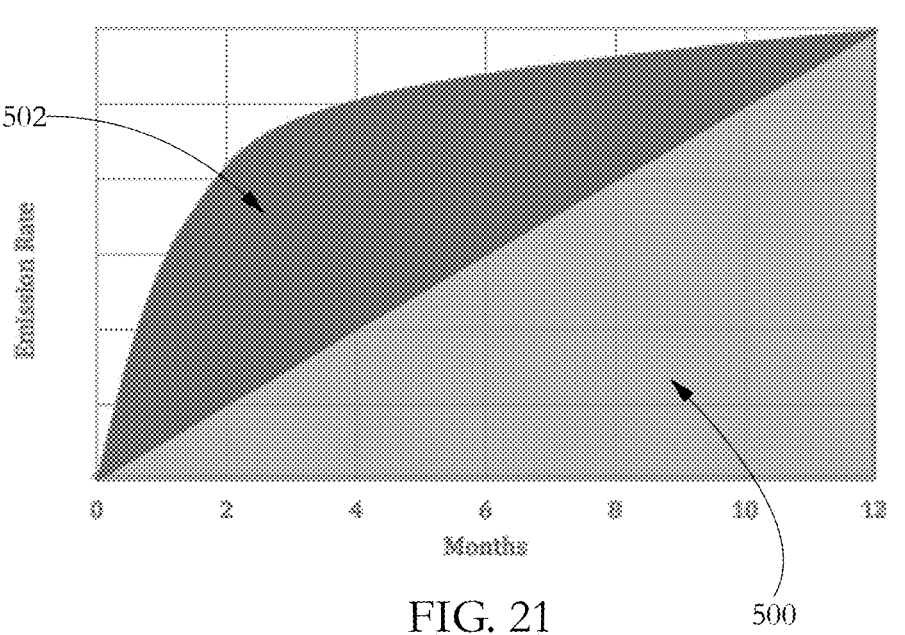
FIG. 21 illustrates an exemplary effect of accelerating repairs on emission reduction according to some embodiments of the present invention.

Leak repairs need not be necessarily performed linearly. For example, repairs may be accelerated, i.e. performed preferentially early in a reporting period. FIG. 21 shows an exemplary effect of accelerating repairs on emission rate reduction, over a reporting period of a year. An illustrated baseline area 500 represents the emission reduction resulting from a linear repair schedule, which yields a linear increase in emission rate reduction (i.e. a linear decrease in emission rate). An illustrated additional area 502 denotes the emission reduction due to an accelerated repair schedule, which performs repairs earlier in the year.

Repairs also impact the number of detected leaks, because some leaks may be repaired before data collection was performed in an area, but still generate emissions during the reporting period before repair. Consider a number of leaks repaired at the time t expressed as:

$$N_{rep}(t) = \int_0^t rep(t) \cdot dt \tag{40}$$

The number of leak repair in the year is:

$$N_{rep} = \int_0^Y rep(t) \cdot dt \tag{41}$$

The area covered by the survey for a short period dt at the time t is:

$$\delta A_i(t) = w(t) \cdot dt \tag{42}$$

and the total area is:

$$A_i = \int_0^Y w(t) \cdot dt \tag{43}$$

If the leaks are repaired randomly across the territory (i.e. without an effort to synchronize them before or after the data collection period), the number of leaks that were repaired before data collection at any point in the system is:

$$\delta N_{rep}^{Done}(t) = \int_0^t rep(t) \cdot dt \cdot \frac{w(t)}{A_i} \cdot dt \tag{44}$$

If rep(t) and w(t) are constant, the number of repaired leaks can be expressed as:

$$N_{rep}^{Done}(t) = N_{rep} \cdot \int_0^t \frac{t}{Y^2} \cdot dt \tag{45}$$

Over the reporting period Y, the number of leaks repaired before data collection is then:

$$N_{rep}^{Done} = \frac{N_{rep}}{2} \tag{46}$$

Thus, in such a scenario half of the repairs are performed before data collection and therefore missed during data collection. The number of leaks found by the system in absence of repair is then:

$$N_f^{ref} = f + \frac{N_{rep}}{2} \tag{47}$$

In some embodiments, this new number is included in the calculations of emissions before repairs. If the survey is performed at constant pace over the year, such an adjustment adds to the computed emissions:

$$\text{Emissions}^{Addition} = \overline{RFR_i} \cdot Y \cdot \frac{N_{rep}}{2} \qquad (48)$$

Thus, if repairs and data collection are performed independently and at constant pace, the reduction of emissions because of repairs exactly balances the effect on emissions of additional leaks missed during data collection. In such a case, emissions calculated without accounting for repairs provides an accurate estimate of emissions determined by accounting for repairs.

In some embodiments, if the data collection and repairs are not performed at a constant pace, the reported emissions are adjusted by integrating numerically the two expressions:

$$\text{Repair}_{reduction} = \overline{RFR_i} \cdot \int_0^Y rep(t) \cdot (Y-t) \cdot dt \qquad (49)$$

$$N_{rep}^{Done}(Y) = \int_0^Y \left[ \int_0^t rep(t) \cdot dt \right] \cdot \frac{w(t)}{A_i} \cdot dt \qquad (50)$$

In some embodiments, a repair schedule may be provided according to leak grade, for example as illustrated below:

TABLE 6

| Leak grade | Repair time frame | Share of total leaks |
|---|---|---|
| 1 | Immediate | 20% |
| 2 | 1 year | 30% |
| 3 | 3 years | 50% |

The impact on emissions of such a repair schedule can be determined by calculating the number of repairs during the reporting period and then by using the method described above.

The number of leaks found before repair can be calculated based on the compliance survey frequency and repair schedule. If the number of repairs is equal to the number of new leaks appearing in the system (steady state), the numbers of repairs can be inferred from the number of leaks found before repair by the data collection process.

Figure 22:
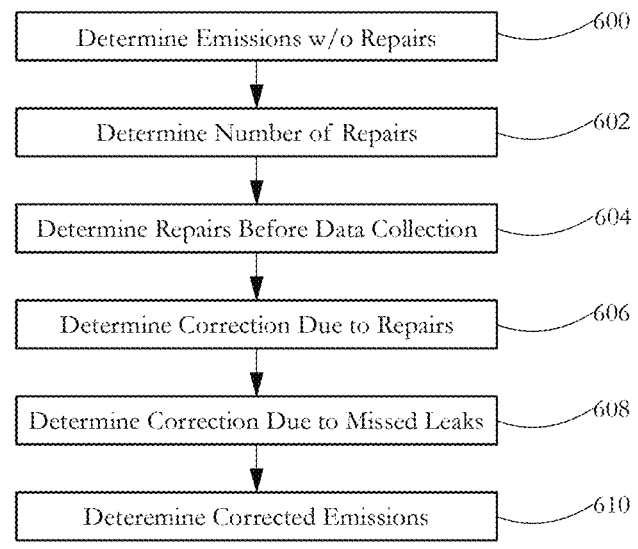
FIG. 22 illustrates an exemplary method of accounting for leak repairs in quantifying emissions over a reporting period according to some embodiments of the present invention.

FIG. 22 shows an exemplary method used to account for repairs according to some embodiments. In a step 600, emissions in the absence of repairs are determined as described above. In a step 602, the number of repairs over the reporting period is determined according to the number of leak survey detections, repair schedule and survey schedule/frequency. In a step 604, the number of repairs before data collection is determined according to the survey and repair schedules. In a step 606, an emission correction due to repairs is determined as described above. In a step 608, an emission correction resulting from missed leaks due to early repairs is determined as described above. In a step 610, the determined emission corrections are added to the emissions in the absence of repairs to generate a corrected emissions value accounting for repairs.

Figure 23:
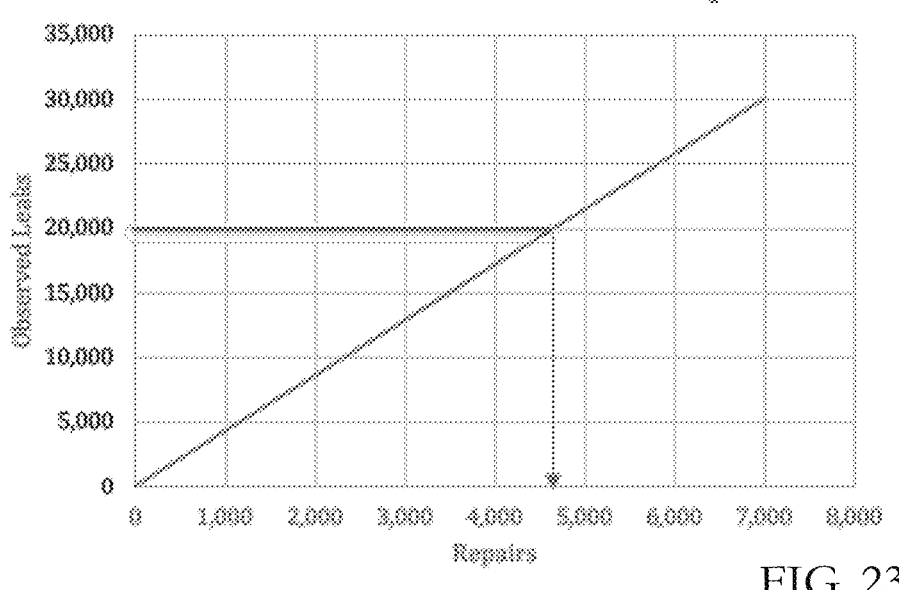
FIG. 23 illustrates an exemplary linear relationship between leak repairs and detected leaks according to some embodiments of the present invention.
Figure 24:
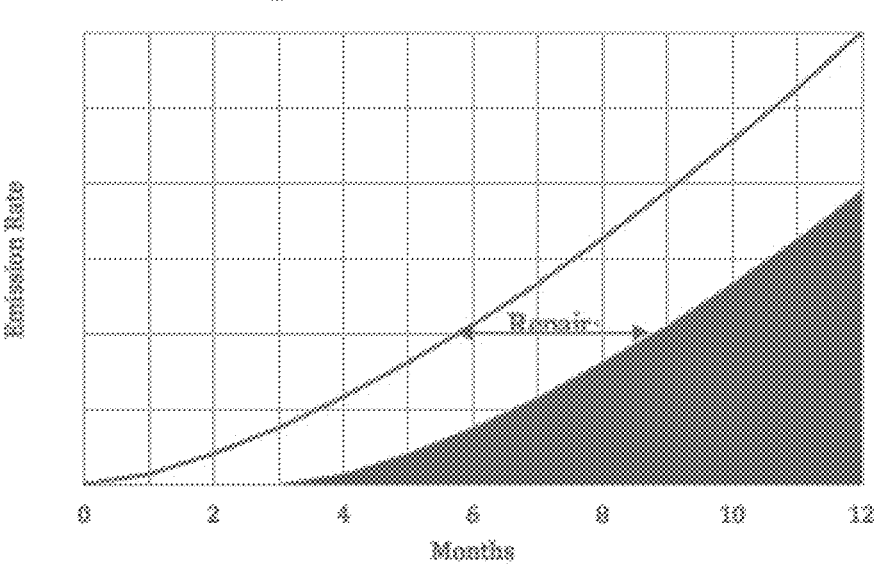
FIG. 24 illustrates an exemplary effect of repairs on emission rate reduction according to some embodiments of the present invention.

FIG. 23 shows an exemplary relationship between number of annual repairs and number of observed leaks for a given repair policy and compliance survey frequency, for data collection performed at a constant pace/rate. As illustrated, the number of repairs increases linearly with the number of detected leaks.

If repairs are triggered by emission data collection (and resulting leak detection), the average delay for repair may be added to the leak detection time. The emission reduction due to repair may then be expressed as:

$$\text{Repair}_{reduction} = \int_0^Y Er(t) \cdot \text{Max}[(Y-t-\text{Delay}), 0] \cdot dt \qquad (51)$$

It will be clear to one skilled in the art that the above embodiments may be altered in many ways without departing from the scope of the invention. For example, gas leaks may include, but are not limited to: leaks from gas pipes or transportation systems (e.g., natural gas leaks), leaks from gas processing or handling facilities, and emissions from gas sources into the environment (e.g., pollution, gas emission from landfills, etc.). Gas concentration measurements are preferably performed rapidly (e.g., at a rate of 0.2 Hz or greater, more preferably 1 Hz or greater, for example 4 Hz or greater). This enables the concept of driving a vehicle at normal surface street speeds (e.g., 35 miles per hour) while accumulating useful gas concentration and wind measurement data. However, embodiments of the invention do not depend critically on the gas detection technology employed. Any gas concentration measurement technique capable of providing gas concentration measurements can be employed in some embodiments.

Although the gas concentration measurements are preferably performed while the gas measurement device is moving, at least some gas concentration measurements can be performed while the gas concentration measurement device is stationary. Such stationary gas concentration measurements may be useful for checking background gas concentrations, for example. While real-time measurements are preferred, post analysis of more sparsely sampled data, e.g., via vacuum flask sampling and later analysis via gas chromatography or other methods, may be used in some embodiments. Optionally, measurements can be made on different sides of the road or in different lanes to provide more precise localization of the leak source. Optionally, the present approaches can be used in conjunction with other conventional methods, such as visual inspection and/or measurements with handheld meters to detect emitted constituents, to further refine the results. Optionally, measurements can be made at reduced speed, or with the vehicle parked near the source, to provide additional information on location and/or source attribution.

Optionally, the system can include a source of atmospheric meteorological information, especially wind direction, but also wind speed or atmospheric stability conditions, either on-board the vehicle or at a nearby location. The stability of the atmospheric conditions can be estimated simply from the wind speed, the time of day, and the degree of cloudiness, all of which are parameters that are available either on the vehicle or from public weather databases. Optionally, the apparatus can include an on-board video camera and logging system that can be used to reject potential sources on the basis of the local imagery collected along with the gas concentration and wind data. For example, a measured emissions spike could be discounted if a vehicle powered by natural gas passed nearby during the measurements. Optionally, repeated measurements of a single location can be made to provide further confirmation (or rejection) of potential leaks.

Accordingly, the scope of the invention should be determined by the following claims and their legal equivalents.

What is claimed is:

1. A system comprising at least one hardware processor and a memory storing instructions which, when executed, cause the system to:

receive collected data including gas concentration and location values collected by a vehicle-borne gas concentration measurement device configured to perform a sequence of geospatially-referenced mobile gas concentration measurements along one or more survey paths within a target area;

identify a set of gas leaks within the target area according to the collected data; and determine a total gas emission quantity emitted within the target area over a time period encompassing the sequence of gas concentration measurements, wherein determining the total gas emission quantity comprises performing a temporal extrapolation of gas emission quantity over at least part of the time period encompassing the sequence of gas concentration measurements.

2. The system of claim 1, wherein performing the temporal extrapolation comprises calculating a cumulative emission of at least one identified leak starting with a time preceding a detection of the at least one identified leak.

3. The system of claim 1, wherein determining the total gas emission quantity comprises performing a spatial extrapolation of gas emission quantity over at least part of the target area not surveyed over the time period.

4. The system of claim 3, wherein performing the spatial extrapolation comprises scaling a gas emission quantity according a fraction of the target area surveyed over the time period.

5. The system of claim 1, wherein determining the total gas emission quantity comprises determining whether identified gas leaks are above ground or below ground, and computing the total gas emission quantity selectively according to gas leaks determined to be below ground.

6. The system of claim 1, wherein determining the total gas emission quantity comprises determining whether at least a subset of the gas leaks have been repaired during the time period.

7. The system of claim 1, wherein the time period is at least one month.

8. The system of claim 1, wherein the instructions further cause the computer system to determine an uncertainty in the determined total gas emission quantity.

9. The system of claim 1, wherein determining the total gas emission quantity comprises binning gas leak emission rates for identified gas leaks by leak rate magnitude.

10. The system of claim 1, wherein determining the total gas emission quantity comprises determining a value of an expression $$\sum_i^{N_i} RFR_i \cdot BGP_i \cdot (\text{Min(End, Repair)} - \text{Start}) +$$

$$\frac{\text{Extent}_{NotSurveyed}}{\text{Extent}_{Surveyed}} \cdot \sum_i^{N_i} RFR_i \cdot BGP_i \cdot (\text{End} - \text{Start}),$$

wherein the index i denotes identified gas leaks, RFR denotes representative flow rate for each identified leak, BGP denotes whether an identified leak is determined to be below-ground, End denotes an end of the time period, Repair denotes a time of repair of an identified gas leak, if any, Start denotes a start of the time period, Extent$_{NotSurveyed}$ denotes an extent of natural gas distribution infrastructure within the target area and not surveyed within the reporting period, and Extent$_{Surveyed}$ denotes an extent of natural gas distribution infrastructure within the target area and surveyed within the reporting period.

11. A method comprising employing a system comprising at least one hardware processor and a memory storing instructions to:

receive collected data including gas concentration and location values collected by a vehicle-borne gas concentration measurement device configured to perform a sequence of geospatially-referenced mobile gas concentration measurements along one or more survey paths within a target area;

identify a set of gas leaks within the target area according to the collected data; and determine a total gas emission quantity emitted within the target area over a time period encompassing the sequence of gas concentration measurements, wherein determining the total gas emission quantity comprises performing a temporal extrapolation of gas emission quantity over at least part of the time period encompassing the sequence of gas concentration measurements.

12. The method of claim 11, wherein performing the temporal extrapolation comprises calculating a cumulative emission of at least one identified leak starting with a time preceding a detection of the at least one identified leak.

13. The method of claim 11, wherein determining the total gas emission quantity comprises performing a spatial extrapolation of gas emission quantity over at least part of the target area not surveyed over the time period.

14. The method of claim 13, wherein performing the spatial extrapolation comprises scaling a gas emission quantity according a fraction of the target area surveyed over the time period.

15. The method of claim 11, wherein determining the total gas emission quantity comprises determining whether identified gas leaks are above ground or below ground, and computing the total gas emission quantity selectively according to gas leaks determined to be below ground.

16. The method of claim 11, wherein determining the total gas emission quantity comprises determining whether at least a subset of the gas leaks have been repaired during the time period.

17. The method of claim 11, wherein the time period is at least one month.

18. The method of claim 11, further comprising employing the system to determine an uncertainty in the determined total gas emission quantity.

19. The method of claim 11, wherein determining the total gas emission quantity comprises binning gas leak emission rates for identified gas leaks by leak rate magnitude.

20. The method of claim 11, wherein determining the total gas emission quantity comprises determining a value of an expression $$\sum_i^{N_i} RFR_i \cdot BGP_i \cdot (\text{Min(End, Repair)} - \text{Start}) +$$

$$\frac{\text{Extent}_{NotSurveyed}}{\text{Extent}_{Surveyed}} \cdot \sum_i^{N_i} RFR_i \cdot BGP_i \cdot (\text{End} - \text{Start}),$$

wherein the index i denotes identified gas leaks, RFR denotes representative flow rate for each identified leak, BGP denotes whether an identified leak is determined to be below-ground, End denotes an end of the time period, Repair denotes a time of repair of an identified gas leak, if any, Start denotes a start of the time period, $\text{Extent}_{NotSurveyed}$ denotes an extent of natural gas distribution infrastructure within the target area and not surveyed within the reporting period, and $\text{Extent}_{Surveyed}$ denotes an extent of natural gas distribution infrastructure within the target area and surveyed within the reporting period.

21. A non-transitory computer-readable medium encoding instructions which, when executed by at least one hardware processor of a computer system, cause the computer system to:

receive collected data including gas concentration and location values collected by a vehicle-borne gas concentration measurement device configured to perform a sequence of geospatially-referenced mobile gas concentration measurements along one or more survey paths within a target area;

identify a set of gas leaks within the target area according to the collected data; and determine a total gas emission quantity emitted within the target area over a time period encompassing the sequence of gas concentration measurements, wherein determining the total gas emission quantity comprises performing a temporal extrapolation of gas emission quantity over at least part of the time period encompassing the sequence of gas concentration measurements.

\* \* \* \* \*